(12) United States Patent
Khosravi et al.

(10) Patent No.: US 9,650,335 B2
(45) Date of Patent: May 16, 2017

(54) COMPOUNDS, MONOMERS, AND POLYMERS CONTAINING A CARBONATE LINKAGE

(75) Inventors: Ezat Khosravi, Gilesgate Moor (GB); Osama M. Musa, Kinnelon, NJ (US)

(73) Assignee: ISP INVESTMENTS LLC, Wilmington, DE (US)

( * ) Notice: Subject to any disclaimer, the term of this patent is extended or adjusted under 35 U.S.C. 154(b) by 834 days.

(21) Appl. No.: 13/980,086

(22) PCT Filed: Jan. 17, 2012

(86) PCT No.: PCT/US2012/021497
§ 371 (c)(1),
(2), (4) Date: Aug. 26, 2013

(87) PCT Pub. No.: WO2012/099847
PCT Pub. Date: Jul. 26, 2012

(65) Prior Publication Data
US 2013/0324687 A1    Dec. 5, 2013

Related U.S. Application Data

(60) Provisional application No. 61/433,392, filed on Jan. 17, 2011.

(51) Int. Cl.
C07D 207/27     (2006.01)
C07D 207/28     (2006.01)
(Continued)

(52) U.S. Cl.
CPC ............ C07D 207/27 (2013.01); C07C 69/96 (2013.01); C07D 205/08 (2013.01);
(Continued)

(58) Field of Classification Search
CPC .. C07D 207/27; C07D 207/26; C07D 207/28; C07D 207/263; C07D 207/267; C07D 205/08; C07D 205/12; C07D 209/10; C07D 209/12; C07D 227/12; C07D 245/00; C07D 245/02; C07D 245/04; C07D 245/06; C07C 303/02; C07C 303/36; C07C 69/54;
(Continued)

(56) References Cited

U.S. PATENT DOCUMENTS

| 4,414,396 | A | | 11/1983 | Boyer | |
|---|---|---|---|---|---|
| 4,515,964 | A | | 5/1985 | Boyer | |
| 5,610,252 | A | * | 3/1997 | Bambury | C07C 69/96 526/245 |

FOREIGN PATENT DOCUMENTS

| CH | EP0252885 A1 * | 1/1988 | ............ C07D 499/88 |

OTHER PUBLICATIONS

CID 22116721 Compound Summary Create date Dec. 5, 2007.
International Search Report, PCT/US2012/021497, published on Jul. 26, 2012.

* cited by examiner

Primary Examiner — Ling Choi
Assistant Examiner — David L Miller
(74) Attorney, Agent, or Firm — William J. Davis

(57) ABSTRACT

The invention provides compounds and monomers having a carbonate linkage. The monomers can be used to form homopolymers or can be coupled with other monomers to provide a wide variety of non-homopolymers. The invention further provides a wide variety of compositions comprising the compounds, monomers, and polymers. In the exemplary structures below, Q, A, R, and n are as described herein.

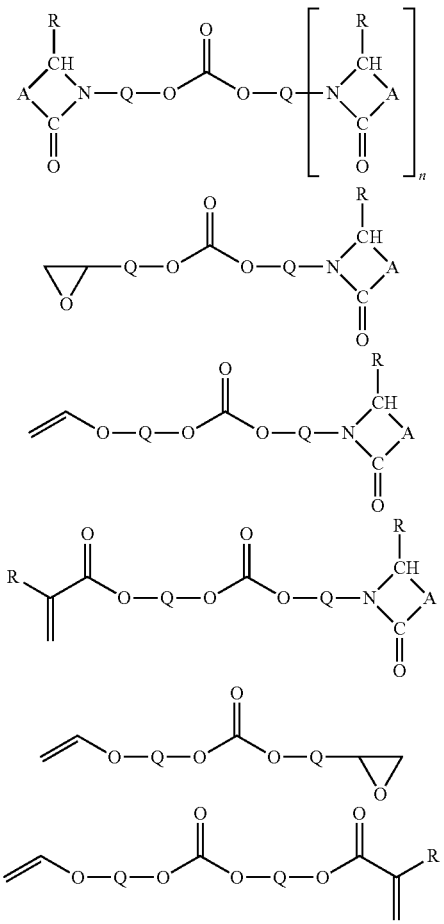

5 Claims, No Drawings

(51) Int. Cl.
*C07D 205/12* (2006.01)
*C07D 207/263* (2006.01)
*C07D 205/08* (2006.01)
*C07D 207/267* (2006.01)
*C07D 207/26* (2006.01)
C08F 220/00 (2006.01)
C07C 69/96 (2006.01)
C08F 26/10 (2006.01)
*C07D 245/02* (2006.01)
*C07D 245/00* (2006.01)
*C07D 245/04* (2006.01)
*C07D 245/06* (2006.01)
*C07D 227/12* (2006.01)
*C07C 303/02* (2006.01)
*C07C 303/36* (2006.01)
*C07C 69/54* (2006.01)
*C08F 26/06* (2006.01)
*C08F 220/34* (2006.01)
*C08F 120/36* (2006.01)
*C08F 126/06* (2006.01)
*C08F 20/36* (2006.01)
*C08F 226/06* (2006.01)

(52) U.S. Cl.
CPC ......... *C07D 205/12* (2013.01); *C07D 207/26* (2013.01); *C07D 207/263* (2013.01); *C07D 207/267* (2013.01); *C07D 207/28* (2013.01); *C08F 26/10* (2013.01); *C08F 220/00* (2013.01); *C07C 69/54* (2013.01); *C07C 303/02* (2013.01); *C07C 303/36* (2013.01); *C07D 227/12* (2013.01); *C07D 245/00* (2013.01); *C07D 245/02* (2013.01); *C07D 245/04* (2013.01); *C07D 245/06* (2013.01); *C08F 20/36* (2013.01); *C08F 26/06* (2013.01); *C08F 120/36* (2013.01); *C08F 126/06* (2013.01); *C08F 226/06* (2013.01); *C08F 2220/346* (2013.01)

(58) Field of Classification Search
CPC .... C07C 69/96; C08F 26/06; C08F 2220/346; C08F 120/36; C08F 20/36; C08F 126/06; C08F 226/06
See application file for complete search history.

COMPOUNDS, MONOMERS, AND POLYMERS CONTAINING A CARBONATE LINKAGE

CROSS REFERENCE TO RELATED APPLICATIONS

This application is the national stage of PCT Application No. PCT/US2012/021497 filed Jan. 17, 2012, which claims priority from Provisional Patent Application No. 61/433,392, filed Jan. 17, 2011, the entire disclosures of which are hereby incorporated in their entirety.

BACKGROUND OF THE INVENTION

Field of the Invention

The present application discloses compounds and monomers having a carbonate linkage. The monomers can be used to form homopolymers or can be coupled with other monomers to provide a wide variety of non-homopolymers. The present application further provides a wide variety of compositions comprising the compounds, monomers, and polymers.

Description of Related Art

U.S. Pat. No. 5,210,332 discloses a process for preparing ethers which comprises contacting a carboxylated ether with a metal oxide catalyst under conditions effective to produce the ether.

U.S. Pat. No. 4,954,553 discloses waterborne phenoxy resins which are blended with modifier resins.

U.S. Pat. No. 3,377,316 discloses polyhydroxyaminoureas of the formula:

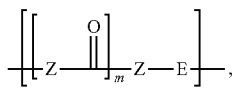

wherein Z is a 1,4-piperazine diradical (1,4-piperazinylene radical), E is a hydroxyl containing radical residuum of an epoxide, and m is an integer from 1 to 2.

U.S. Pat. No. 4,237,250 discloses polyurethanes containing sulfonic acid ester groups, characterized by aryl sulfonic acid alkyl ester groups attached to aromatic nuclei as chain members.

U.S. Pat. No. 3,821,160 discloses thermoplastic polyhydroxy-ethers having improved stress-crack resistance properties. The "thermoplastic polyhydroxy-ethers" are disclosed to be substantially liner polymers having the general formula:

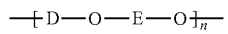

wherein D is the radical residuum of a dihydric phenol, E is a hydroxyl containing radical residuum of an epoxide, and n represents the degree of polymerization and is at least 30 and is preferably 80 or more.

U.S. Pat. No. 2,795,572 discloses epoxy-substituted organic compounds, more particularly, epoxy-esters of carbonic acids, methods of preparation thereof, and utilization of the esters, particularly as stabilizers and plasticizers, and as monomers for the preparation of improved polymeric products.

U.S. Pat. No. 5,159,098 discloses alk-1-enyloxy carbamates which are rapidly curable by cationic radiation, and the use of these products as protective coatings, reactive diluents for other polymerizable compounds, and as photoresist materials.

A process for preparation of cyclic carbonates by reaction of alkali metal carbonates with epihalohydrins is described by Gabriel Rokicki and Witold Kuran in *Bulletin of Chemical Society of Japan*, 1984, 57, 1662-1666.

Degradable compounds, monomers, and polymers are substances that can be degraded in a biological or non-biological environment. Because of the increasing use of polymers in disposable items, drug delivery systems, and tissue regeneration scaffolds, there is a need for compounds, monomers, and polymers that are degradable.

Methods to develop degradable polymers include modifying existing degradable monomers to add functionality to provide desirable properties. A useful degradable functional group is the carbonate linkage,

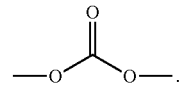

Carbonate linkages in organic compounds, such as carbonate esters, can be employed as degradable functional groups because they can be converted to carbon dioxide. The carbonate linkage, or group, can be introduced into a compound through the use of the coupling agent 1,1'-carbonyldiimidazole (CDI):

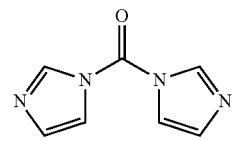 [SMILES: O=C(n1ccnc1)n1ccnc1]

1,1'-Carbonyldiimidazole is a useful coupling agent because it is very reactive towards nucleophiles. The coupling ability of 1,1'-carbonyldiimidazole may be used to prepare degradable compounds containing a carbonate linkage.

The degradable monomers contain a carbonate linkage that can be used to form homopolymers or can be coupled with other monomers to provide, through the use of polymerization initiators, a wide variety of functionalized polymers.

Modification of degradable compounds with various functional groups can provide polymers having different physical or mechanical properties useful in a wide variety of compositions. The resulting modification of the physical or mechanical properties will depend upon the nature of the functional group and/or mixture of functional groups. Accordingly, there is a need for degradable polymers, resulting from modification of degradable compounds, to alter or improve the physical and mechanical properties of such degradable polymers.

SUMMARY

In accordance with one aspect, the present application provides compounds having the structure set out below:

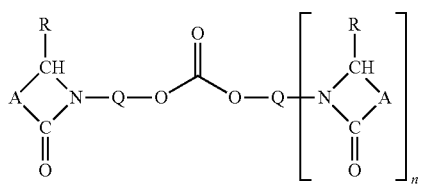

wherein each Q is independently selected from the group consisting of functionalized and unfunctionalized alkylene, cycloalkylene, alkenylene, and arylene groups, wherein any of the groups may be with or without heteroatoms; each A is independently a functionalized or unfunctionalized alkylene or alkenylene group comprising 2 to 50 carbon atoms, wherein 2 to 4 carbon atoms reside in the lactam ring between the

group and the

group; each R is independently selected from the group consisting of hydrogen, functionalized and unfunctionalized alkyl, cycloalkyl, alkenyl, and aryl groups, wherein any of the groups may be with or without heteroatoms; and n is 0 or 1. When n=0, the lactam group is replaced by an R group having the same definition as set forth above.

More specifically, in accordance with the first embodiment, the present application provides a compound having one of the following structures:

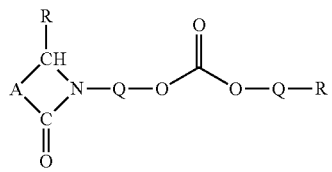
(I)

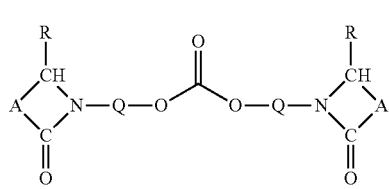
(II)

wherein A, Q and R are as defined above.

In accordance with another aspect, the present application also provides compounds having the structure:

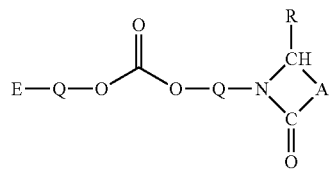

wherein E is a polymerizable moiety and is selected from the group consisting of: anhydrides, vinyl amides, acrylates, styrenes, maleimides, maleates, fumarates, cinnamyls, vinyl imidazoles, vinyl pyridines, vinyl acetates, acrylamides, vinyl sulfones, vinyl carbonates, vinyl-2-pyrrolidones, vinyl lactams, vinyl carbamates, vinyl siloxanes, vinyl ureas, vinyl thiocarbamates, vinyl silanes, vinyl acrylamides, allyl derivatives, vinyl ethers, vinyl oxy, epoxides, oxetanes, benzoxazines, oxazolines, and mixtures thereof; each Q is independently selected from the group consisting of functionalized and unfunctionalized alkylene, cycloalkylene, alkenylene, and arylene groups, wherein any of the groups may be with or without heteroatoms; A is a functionalized or unfunctionalized alkylene or alkenylene group comprising 2 to 50 carbon atoms, wherein 2 to 4 carbon atoms reside in the lactam ring between the

group and the

group; and each R is selected from the group consisting of hydrogen, functionalized and unfunctionalized alkyl, cycloalkyl, alkenyl, and aryl groups, wherein any of the groups may be with or without heteroatoms.

In accordance with yet another aspect, the present application further provides compounds having the structure:

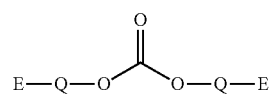

wherein each E is a polymerizable moiety independently selected from the group consisting of: anhydrides, vinyl amides, acrylates, styrenes, maleimides, maleates, fumarates, cinnamyls, vinyl imidazoles, vinyl pyridines, vinyl acetates, acrylamides, vinyl sulfones, vinyl carbonates, vinyl-2-pyrrolidones, vinyl lactams, vinyl carbamates, vinyl siloxanes, vinyl ureas, vinyl thiocarbamates, vinyl silanes, vinyl acrylamides, allyl derivatives, vinyl ethers, vinyl oxy, epoxides, oxetanes, benzoxazines, oxazolines, and mixtures thereof; and each Q is independently selected from the group consisting of functionalized and unfunctionalized alkylene, cycloalkylene, alkenylene, and arylene groups, wherein any of the groups may be with or without heteroatoms, with the proviso that said compound is not

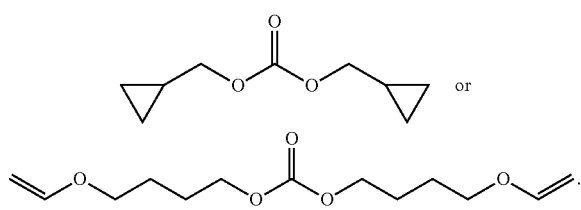

The present application further provides a wide variety of compositions comprising the above-modified compounds. Such compositions include, but are not limited to personal care (e.g., hair care, sun care, skin care, color cosmetic, and oral care), adhesives, coatings, paints, electronics, Household, Industrial and Institutional (HI&I) compositions, inks, membranes, metal working fluids, oilfield chemicals, plastics and plasticizers, textiles, industrial products, biocides, pharmaceuticals/nutritionals, and agrochemical compositions.

DETAILED DESCRIPTION

The present application discloses compounds, monomers, and polymers. The monomers contain a carbonate linkage that can be used to form homopolymers or can be coupled with other monomers to provide a wide variety of polymers. Modification of the compounds with various functional groups can provide polymers having different physical or mechanical properties useful in a wide variety of compositions. The resulting modification of the physical or mechanical properties will depend upon the nature of the functional group and/or mixture of functional groups. The invention further provides a wide variety of compositions comprising the compounds, monomers, and polymers.

In one embodiment, the compounds, monomers, and polymers of the invention are degradable.

The invention provides a wide variety of compositions comprising the compounds, monomers, and polymers including adhesives, aerosols, agricultural compositions, beverages, cleaning compositions, coating compositions, cosmetic formulations, dental compositions, detergents, drugs, encapsulations, foods, hair sprays, lithographic solutions, membrane formulations, oilfield formulations, personal care compositions, pharmaceuticals, pigment dispersions, drug delivery systems, tissue regeneration scaffolds, and the like. Personal care compositions refer to such illustrative non-limiting compositions as skin, sun, oil, hair, cosmetic, and preservative compositions, including those to alter the color and appearance of the skin. Other personal care compositions include, but are not limited to, modified natural oils for increased flexibility in styling, durable styling, increased humidity resistance for hair, skin, and color cosmetics, sun care water-proof/resistance, wear-resistance, shower gels, shampoos, and thermal protecting/enhancing compositions. Dental personal care compositions include denture adhesives, toothpastes, mouth washes, and the like. Pharmaceutical compositions include tablet coatings, tablet binders, transdermal patches, and the like.

As used herein, the following terms have the meanings set out below.

The term "compound" refers to organic molecules comprising at least one carbonate linkage. Examples of these compounds include molecules, homopolymers, monomers, and non-homopolymers. The monomers may be polymerized to form a wide variety of polymers.

The term "degradable" refers to compounds, monomers, and polymers which are degradable in a biological or non-biological environment.

The term "branched and unbranched alkyl groups" refers to alkyl groups, which may be straight chained or branched. For example, the alkyl groups may have from 1 to about 18 carbon atoms, more particularly, from 1 to 10 carbon atoms, and yet more particularly from 1 to 6 carbon atoms. Branched groups include isopropyl, tert-butyl, and the like.

The term "carbonate linkage" refers to the carbonate moiety:

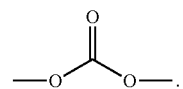

Many different examples of compounds having a carbonate linkage are envisioned, including those described herein. One example is a carbonate ester having the structure:

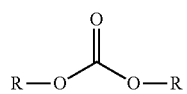

wherein each R is independently selected from the group consisting of hydrogen, functionalized and unfunctionalized alkyl, cycloalkyl, alkenyl, aryl groups, and the like. Additional examples of compounds having at least one carbonate linkage are described herein.

The term "1,1'-carbonyldiimidazole" (CDI) refers to

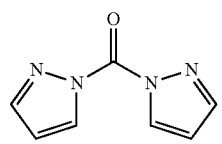 [SMILES: O=C(n1cccn1)n1cccn1]

and its analogues. CDI is one example of a coupling agent because it is reactive with nucleophiles and provides a wide variety of compounds having the carbonate linkage.

The term "polymerization" refers to methods for chemically reacting monomer compounds to form polymer chains. The polymer chain may be alternating, blocked, or random. The type of polymerization method may be selected from a wide variety of methods, and include the following non-limiting examples: free radical polymerization methods such as classical radical polymerization and controlled radical polymerization, Nitroxide Mediation Polymerization (NMP), Atom Transfer Radical Polymerization (ATRP), and Reversible Addition Fragmentation Chain-Transfer (RAFT).

The term "polymer" refers to a large molecule (macromolecule) composed of repeating structural units (monomers) connected by covalent chemical bonds.

The term "homopolymer" refers to polymers polymerized from one type of repeating structural unit (monomer).

The term "copolymer" refers to a polymer polymerized from more than one type of repeating structural units (monomers).

The term "(meth)acrylate" refers to both acrylate and methacrylate. Similarly, the term "(meth)acrylamide" refers to both acrylamide and methacrylamide.

The term "epoxide" refers to groups having the structure:

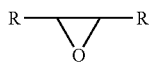

Epoxides are highly strained cyclic ethers that are highly reactive to ring-opening reactions. Each R is independently selected from the group consisting of hydrogen, functionalized and unfunctionalized alkyl, cycloalkyl, alkenyl, aryl groups, and the like.

The term "heteroatom" refers to atoms such as oxygen, nitrogen, sulfur, and phosphorous.

The term "lactam" refers to groups having the structure:

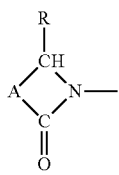

wherein A is a functionalized or unfunctionalized alkylene or alkenylene group comprising 2 to 50 carbon atoms, wherein 2 to 4 carbon atoms reside in the lactam ring between the

group and the

group; and R is selected from the group consisting of hydrogen, functionalized and unfunctionalized alkyl, cycloalkyl, alkenyl, and aryl groups, wherein any of the groups may be with or without heteroatoms.

The term "personal care composition" refers to a composition intended for use on or in the human body and may be an oral care composition, a hair care composition, a hair styling composition, a face care composition, a lip care composition, an eye care composition, a foot care composition, a nail care composition, a sun care composition, a deodorant composition, an antiperspirant composition, a cosmetic composition (including color cosmetics), a skin cleaning composition, an insect repellant composition, a shaving composition, a toothpaste, a mouthwash, a tooth whitener, a tooth stain remover, and/or a hygiene composition. Among their many uses, hair care and hair styling compositions find application in enhancing hair shine, cleansing hair, conditioning hair, repairing split ends, enhancing hair manageability, modulating hair stylability, protecting hair from thermal damage, imparting humidity resistance to hair and hair styles, promoting hair style durability, changing the hair color, straightening and/or relaxing hair, and/or providing protection from UV-A and/or UV-B radiation. Other personal care compositions, such as those for skin care and sun care compositions, are useful for protecting from UV-A and/or UV-B radiation, imparting water resistance or water proofness, moisturizing skin, decreasing and/or minimizing the appearance of wrinkles, firming skin, decreasing or minimizing the appearance of skin blemishes (such as lentigo, skin discolorations, pimples, or acne), changing skin color (such as color cosmetics for the face, cheeks, eyelids, or eye lashes). Oral care compositions according to the invention may be used as denture adhesives, toothpastes, mouthwashes, tooth whiteners, and/or stain removers. Personal care compositions also are used for delivering an active (such as to the skin, hair, or oral cavity).

In a first embodiment, the invention provides compounds having the structure set out below:

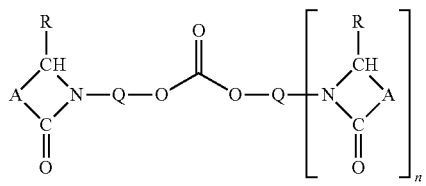

wherein each Q is independently selected from the group consisting of functionalized and unfunctionalized alkylene, cycloalkylene, alkenylene, and arylene groups, wherein any of the groups may be with or without heteroatoms; each A is independently a functionalized or unfunctionalized alkylene or alkenylene group comprising 2 to 50 carbon atoms, wherein 2 to 4 carbon atoms reside in the lactam ring between the

group and the

group; each R is independently selected from the group consisting of hydrogen, functionalized and unfunctionalized alkyl, cycloalkyl, alkenyl, and aryl groups, wherein any of the groups may be with or without heteroatoms; and n is 0 or 1.

More particularly, each Q is independently selected from the group consisting of functionalized and unfunctionalized alkylene, cycloalkylene, alkenylene, and arylene groups containing 1-10 carbon atoms, wherein any of the groups may be with or without heteroatoms. Yet more particularly, each Q is independently selected from the group consisting of 1-8 carbon atoms. Most particularly, each Q is independently selected from the group consisting of 1-6 carbon atoms.

More particularly, each A in the lactam ring between the

group and the $$\underset{\underset{CH}{|}}{\overset{R}{\diagup\diagdown}}$$

group may be independently selected from the group consisting of $$-\overset{H_2}{C}-\overset{H_2}{C}-, \quad -\overset{H_2}{C}-\overset{H_2}{C}-\overset{H_2}{C}-, \quad \text{and}$$
(ethylene)  (propylene)

$$-\overset{H_2}{C}-\overset{H_2}{C}-\overset{H_2}{C}-\overset{H_2}{C}-.$$
(butylene)

More particularly, each A in the lactam ring between the $$\underset{\underset{O}{\|}}{\overset{\diagup}{C}}$$

group and the $$\underset{\underset{CH}{|}}{\overset{R}{\diagup\diagdown}}$$

group may be independently $$-\overset{H_2}{C}-\overset{H_2}{C}- \quad \text{or} \quad -\overset{H_2}{C}-\overset{H_2}{C}-\overset{H_2}{C}-\overset{H_2}{C}-.$$

More particularly, each R may be independently selected from the group consisting of hydrogen, functionalized and unfunctionalized alkyl, cycloalkyl, alkenyl, and aryl groups containing 1-10 carbon atoms, wherein any of the groups may be with or without heteroatoms. More particularly, each R may be independently selected from the group consisting of 1-8 carbon atoms. Most particularly, each R may be independently selected from the group consisting of 1-6 carbon atoms.

In another aspect of the first embodiment, the carbonate may be represented by the structure

[Structure showing lactam ring with R, CH, A, N-Q-O-C(=O)-O-Q-R]

wherein each Q is independently selected from the group consisting of functionalized and unfunctionalized alkylene, cycloalkylene, alkenylene, and arylene groups, wherein any of the groups may be with or without heteroatoms; A is independently a functionalized or unfunctionalized alkylene or alkenylene group comprising 2 to 50 carbon atoms, wherein 2 to 4 carbon atoms reside in the lactam ring between the $$\underset{\underset{O}{\|}}{\overset{\diagup}{C}}$$

group and the $$\underset{\underset{CH}{|}}{\overset{R}{\diagup\diagdown}}$$

group; and each R is independently selected from the group consisting of hydrogen, functionalized and unfunctionalized alkyl, cycloalkyl, alkenyl, and aryl groups, wherein any of the groups may be with or without heteroatoms.

As a non-limiting example, these compounds may be produced by the reaction of 1,1'-carbonyldiimidazole and two alcohols, one of which is a lactam-containing alcohol:

[Reaction scheme showing carbonyldiimidazole + HO—Q—R + lactam alcohol → carbonate product]

wherein Q, R, and A retain the definitions immediately set forth above.

Examples of compounds according to the first embodiment include, but are not limited to:

[Structure of bis(pyrrolidinone-ethyl) carbonate], and

[Structure of pyrrolidinone-ethyl butyl carbonate].

In a second embodiment, the invention provides compounds having the structure:

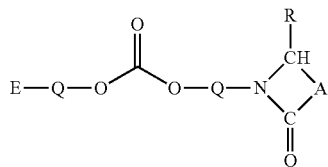

wherein E is a polymerizable moiety selected from the group consisting of: anhydrides, vinyl amides, acrylates, styrenes, maleimides, maleates, fumarates, cinnamyls, vinyl imidazoles, vinyl pyridines, vinyl acetates, acrylamides, vinyl sulfones, vinyl carbonates, vinyl-2-pyrrolidones, vinyl lactams, vinyl carbamates, vinyl siloxanes, vinyl ureas, vinyl thiocarbamates, vinyl silanes, vinyl acrylamides, allyl derivatives, vinyl ethers, vinyl oxy, epoxides, oxetanes, benzoxazines, oxazolines, and mixtures thereof; each Q is independently selected from the group consisting of functionalized and unfunctionalized alkylene, cycloalkylene, alkenylene, and arylene groups, wherein any of the groups may be with or without heteroatoms; A is a functionalized or unfunctionalized alkylene or alkenylene group comprising 2 to 50 carbon atoms, wherein 2 to 4 carbon atoms reside in the lactam ring between the

group and the

group; and each R is selected from the group consisting of hydrogen, functionalized and unfunctionalized alkyl, cycloalkyl, alkenyl, and aryl groups, wherein any of the groups may be with or without heteroatoms.

Three non-limiting examples of this second embodiment are the compounds represented by the structures:

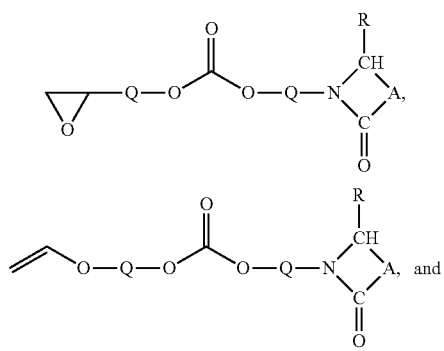

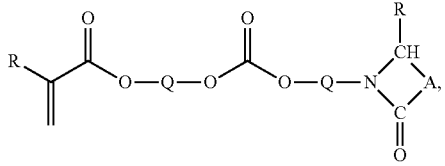

for which: each R is independently selected from the group consisting of hydrogen, functionalized and unfunctionalized alkyl, cycloalkyl, alkenyl, and aryl groups containing 1-10 carbon atoms, wherein any of the groups may be with or without heteroatoms; said A is selected from the group consisting of

and each Q is independently selected from the group consisting of functionalized and unfunctionalized alkylene, cycloalkylene, alkenylene, and arylene groups containing 1-10 carbon atoms, wherein any of the groups may be with or without heteroatoms.

Examples of this second embodiment include, without limitation, the following compounds:

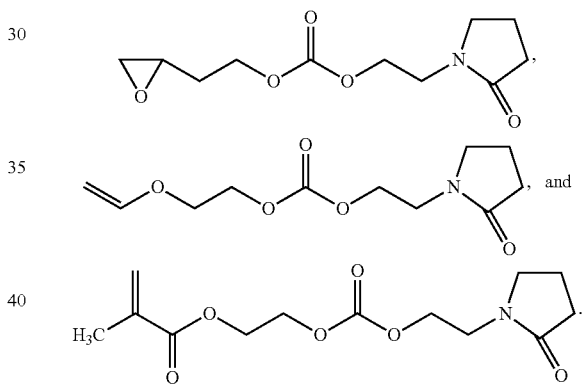

In yet a third embodiment, the invention provides compounds having the structure:

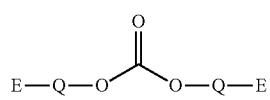

wherein each E is a polymerizable moiety independently selected from the group consisting of: anhydrides, vinyl amides, acrylates, styrenes, maleimides, maleates, fumarates, cinnamyls, vinyl imidazoles, vinyl pyridines, vinyl acetates, acrylamides, vinyl sulfones, vinyl carbonates, vinyl-2-pyrrolidones, vinyl lactams, vinyl carbamates, vinyl siloxanes, vinyl ureas, vinyl thiocarbamates, vinyl silanes, vinyl acrylamides, allyl derivatives, vinyl ethers, vinyl oxy, epoxides, oxetanes, benzoxazines, oxazolines, and mixtures thereof; and each Q is independently selected from the group consisting of functionalized and unfunctionalized alkylene, cycloalkylene, alkenylene, and arylene groups, wherein any of the groups may be with or without heteroatoms, with the proviso that said compound is not

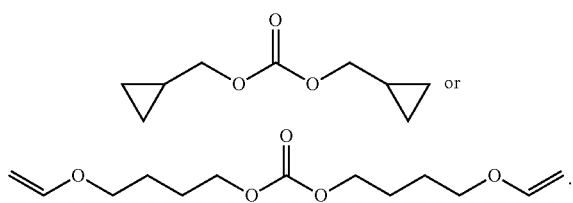 or

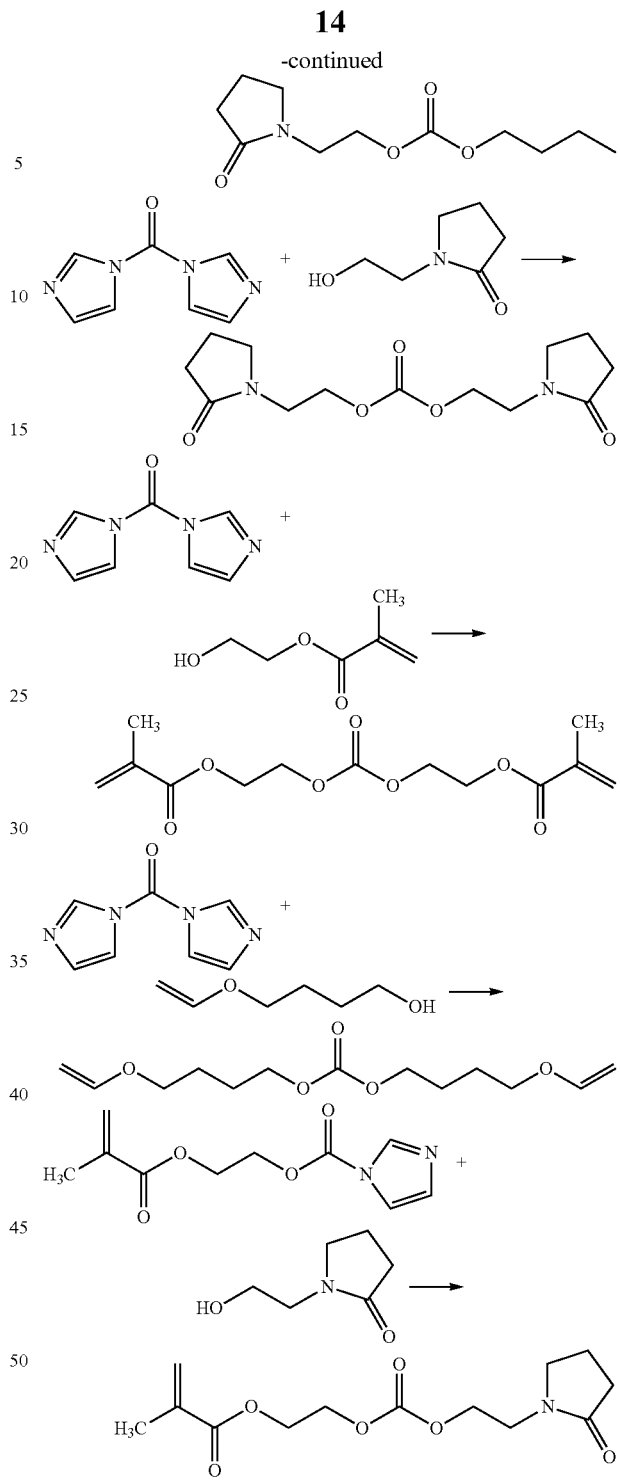

More particularly, the compounds of the third embodiment may be represented by the structures:

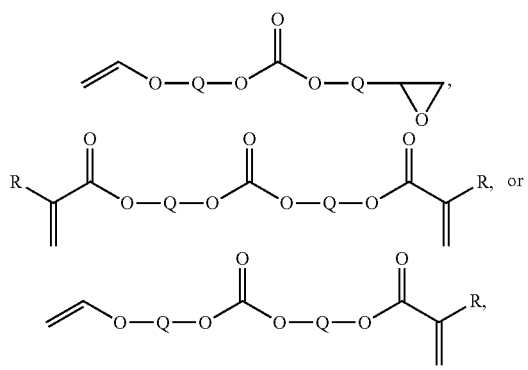

wherein: each R is independently selected from the group consisting of hydrogen, functionalized and unfunctionalized alkyl, cycloalkyl, alkenyl, and aryl groups containing 1-10 carbon atoms, wherein any of the groups may be with or without heteroatoms; and each Q is independently selected from the group consisting of functionalized and unfunctionalized alkylene, cycloalkylene, alkenylene, and arylene groups containing 1-10 carbon atoms, wherein any of the groups may be with or without heteroatoms.

For example, the third embodiment provides the following compound:

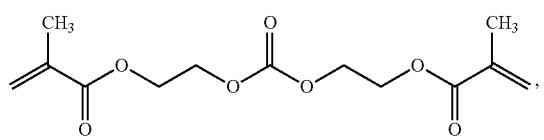 [SMILES: C=C(C)C(=O)OCCOC(=O)OCCOC(=O)C(=C)C]

and others may be recognized by one skilled in the art as pertaining to this embodiment.

The invention further provides a wide variety of compositions comprising the above-modified compounds.

Non-limiting illustrative examples of structures of compounds of the invention containing a carbonate linkage, prepared as set out below, include the following:

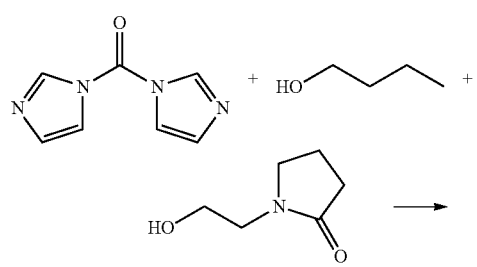

As set out above, the above embodiments describe compounds having a carbonate linkage. Carbonate-containing compounds may exhibit degradability in biological or non-biological environments. Nonetheless, degradability is not a limitation of the invention, inasmuch as the compounds exhibit functional utility apart from degradability. Consider the monomers, which can be used to form a wide variety of polymers, including homopolymers and non-homopolymers.

The type of polymerization method utilized to create these polymers may be selected from a wide variety of methods.

Examples include, but are not limited to, radical polymerization methods and controlled radical polymerization including Nitroxide Mediation Polymerization (NMP), Atom Transfer Radical Polymerization (ATRP), and Reversible Addition Fragmentation Chain-Transfer (RAFT).

In another aspect, the invention provides a wide variety of compositions comprising the compounds, monomers, and polymers described herein. Such compositions include, but are not limited to, personal care (e.g., hair care, sun care, skin care, oral care), adhesives, coatings, paints, electronics, Household, Industrial and Institutional (HI&I) compositions, inks, membranes, metal working fluids, oilfield chemicals, plastics and plasticizers, textiles, industrial products, biocides, pharmaceuticals/nutritionals, and agrochemical compositions.

Non-limiting illustrative examples of structures of homopolymers of the invention, prepared from monomers containing a carbonate linkage, prepared as set out below, include the following:

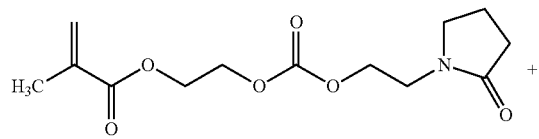

+

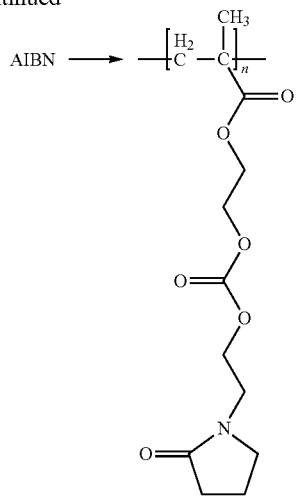

Controlled radical homopolymerization of the HEMA-HEP carbonate monomer using Reversible Addition-Fragmentation Chain Transfer Polymerization (RAFT):

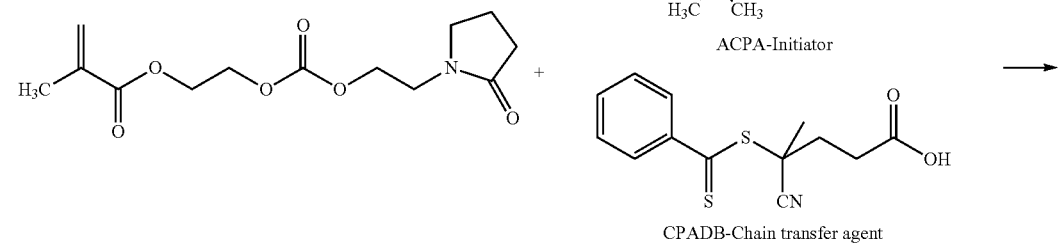

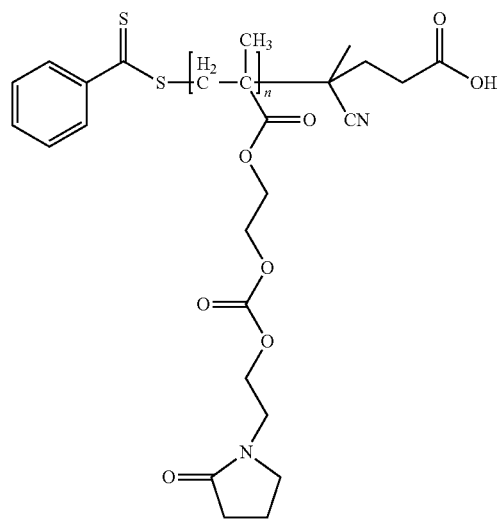

Additionally, the invention further embraces non-homopolymers having one or more of the monomers described herein. These non-homopolymers may be polymerized from at least: (A) a carbonate-containing monomer as detailed above, and (B) a comonomer different from (A), wherein the non-homopolymer is a random, block, or alternating non-homopolymer. Many suitable comonomers are known and suitable with the carbonate-containing monomers described herein, and include the following non-limiting monomer classifications: 4- or 5-substituted-1,2,3-triazoles comprising at least one remote polymerizable moiety, (meth)acrylamides, (meth)acrylates, olefins, allyls, anhydrides, cinnamyls, fumarates, maleates, maleimides, α,β-olefinically unsaturated carboxylic nitriles, styrenes, vinyl esters, vinyl acetates, vinyl amides, vinyl alcohols, vinyl carbonates, vinyl carbamates, vinyl thiocarbamates, vinyl ureas, vinyl ethers, vinyl halides, vinyl imidazoles, vinyl lactams, vinyl pyridines, vinyl silanes, vinyl sulfones, benzoxazines, epoxides, oxazolines, oxetanes, and combinations thereof.

The 4- or 5-substituted-1,2,3-triazoles comprising at least one remote polymerizable moiety are described in copending international application WO 2011/005806, the contents of which are hereby incorporated by reference.

Other comonomers that may be used to synthesize non-homopolymers include the following non-limiting examples:

Comonomers that may be used for the creation of non-homopolymers include, but are not limited to:

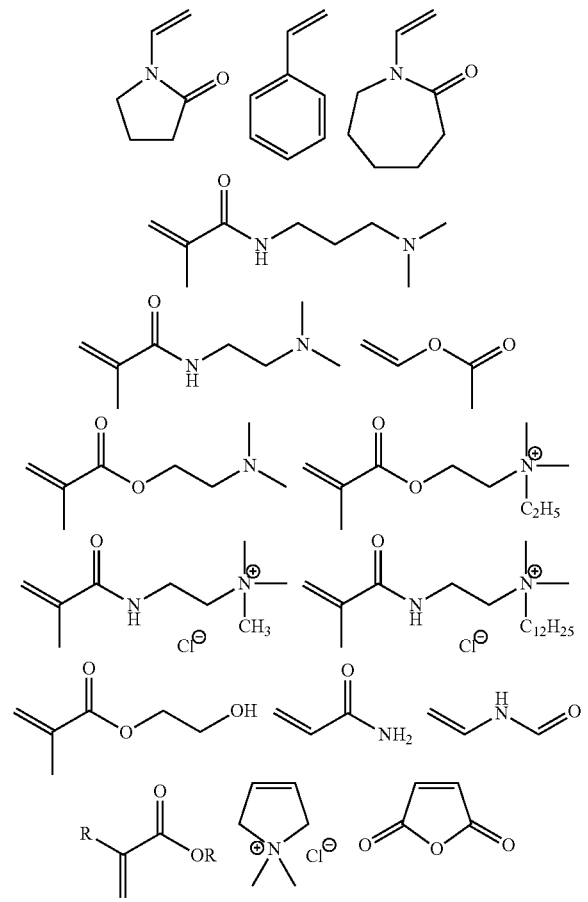

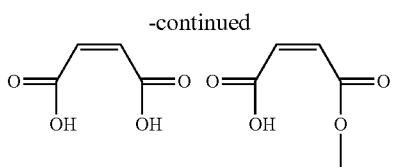

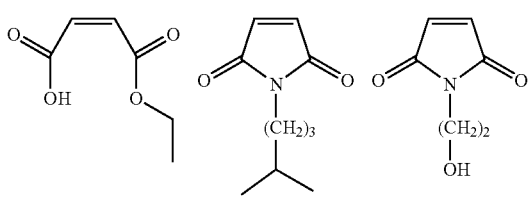

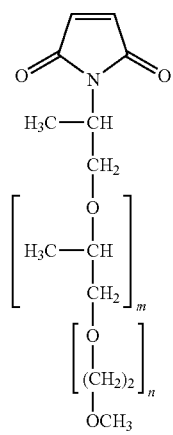

wherein R is independently selected from the group consisting of hydrogen, and functionalized and unfunctionalized alkyl, cycloalkyl, alkenyl, and aryl groups, wherein any of the beforementioned groups may be with or without heteroatoms, and m and n are integers greater than or equal to 1. For example, the list of possible comonomers includes (meth)acrylates and (meth)acrylamides, and other comonomers, shown and not shown, are contemplated.

Random co-polymerization of the HEMA-HEP carbonate monomer with vinyl acetate (VAc):

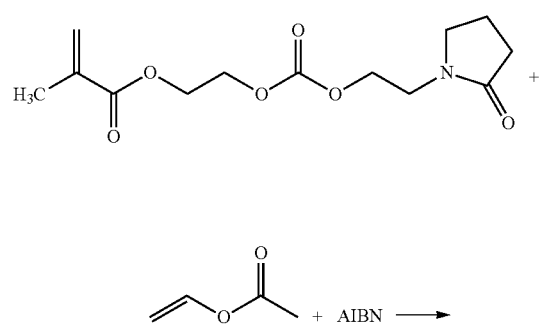

-continued
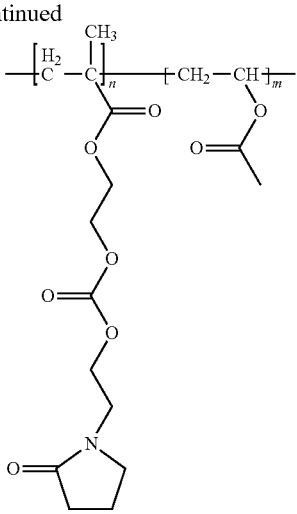
Random co-polymerization of the HEMA-HEP carbonate monomer and N-vinyl-2-caprolactam (NVCL):
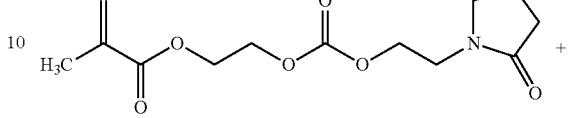
Random co-polymerization of the HEMA-HEP carbonate monomer with N-vinyl-2-pyrrolidone (NVP):
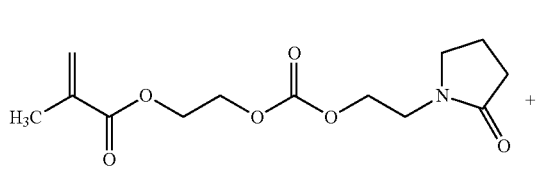
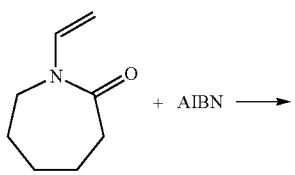
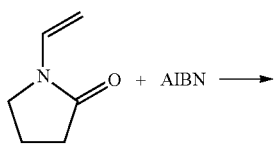
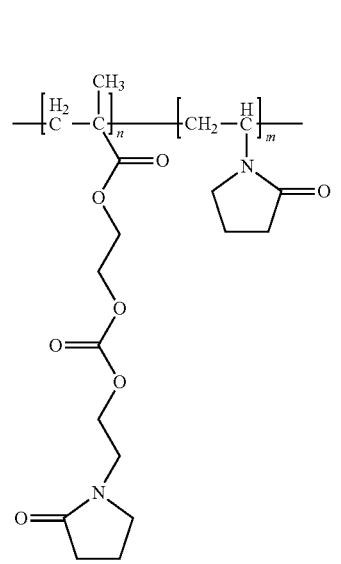
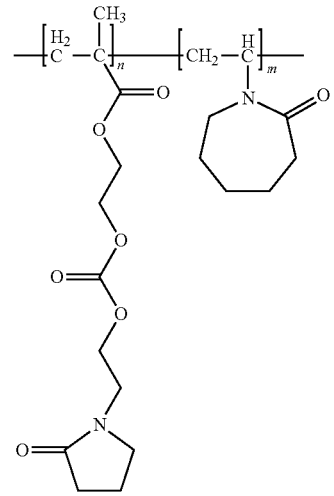
Block co-polymerization of the HEMA-HEP carbonate monomer with poly(N-vinyl-2-pyrrolidone (PVP):

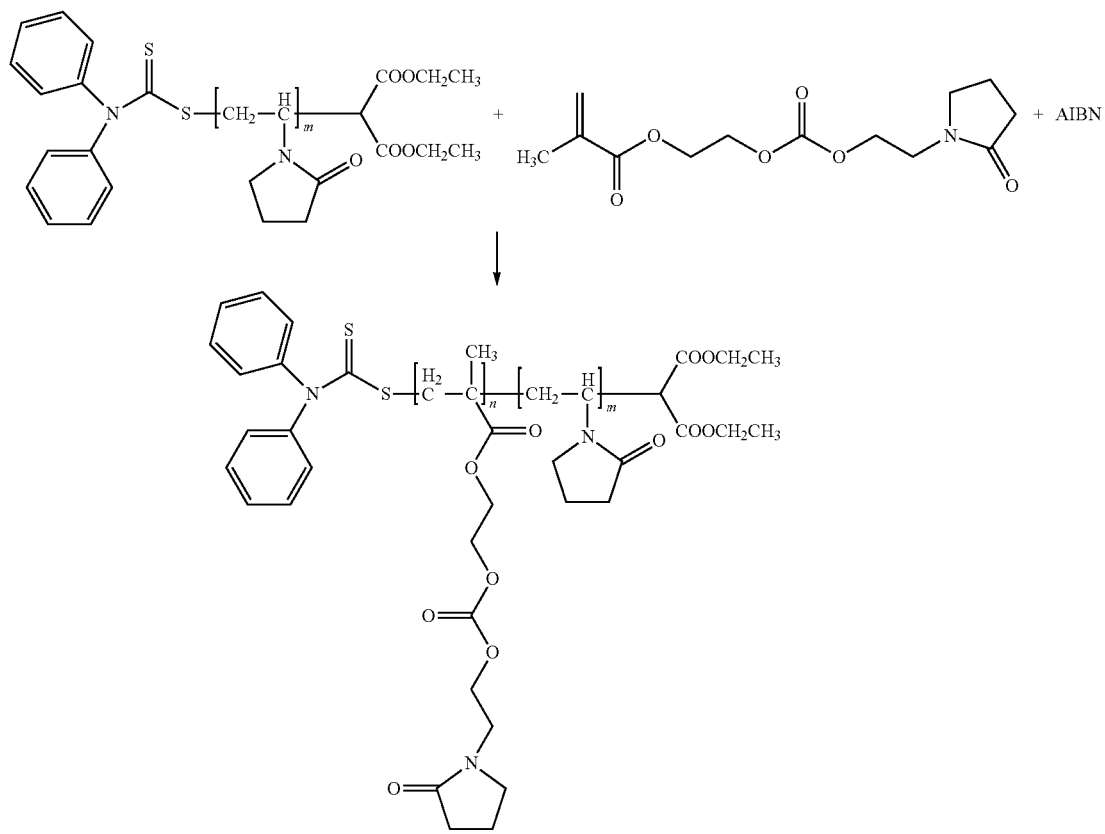

The invention further provides a wide variety of compositions comprising the above-modified degradable compounds.

Description of Compositions Comprising the Compounds, Monomers, and Polymers According to the Present Application The compounds, monomers, and polymers described herein may be used alone or in combination with other ingredient(s) in various compositions and product forms. Such compositions include, but are not limited to, personal care compositions, adhesives, coatings, paints, electronics, Household, Industrial and Institutional (HI&I) compositions, inks, membranes, metal working fluids, oilfield chemicals, plastics and plasticizers, textiles, industrial products, biocides, pharmaceuticals/nutritionals, and agrochemical compositions.

The term "personal care composition" refers to a composition intended for use on or in the human body. Non-limiting, but specific types of personal care compositions include hair care compositions (encompassing styling and non-styling compositions), sun care compositions (encompassing after-sun compositions), skin care compositions, and oral care compositions.

Non-limiting applications of the sun care compositions include: protecting skin and/or hair from UV radiation (including any or all of UV-A, UV-B and/or UV-C radiation), sun screening, skin anti-irritating, skin repairing, skin wrinkle masking, skin nourishing, skin moisturizing, skin relaxing, skin refreshing, skin cooling, skin soothing, skin tanning, skin tan prolonging, sun-less skin tanning, skin glowing, skin micro-glittering, skin shimmering, and skin anti-tanning.

Non-limiting applications of the skin care compositions include: protecting skin from UV radiation (including any or all of UV-A, UV-B and/or UV-C radiation), skin cleansing, face cleansing, body cleansing, insect repelling, antiperspirant, exfoliating skin, rejuvenating skin, influencing cell turnover, deodorant, astringent, imparting water resistance or water proofness to skin, decreasing and/or minimizing the appearance of skin wrinkles, decreasing and/or minimizing the appearance of skin blemishes (such as lentigo, skin discolorations, pimples, and/or acne), changing skin color (including skin lightening, skin brightening, skin color darkening, and color cosmetics for the face, cheeks, lips, eyelids, and/or eye lashes), skin iridescing, skin glossing, curling of eye lashes, eye lining, eye shadowing, mascara, removing facial and/or body hair, skin tightening, skin tanning, skin bronzing, skin blushing, prolonging skin tan, sun-less skin tanning, anti-tanning, skin anti-bacterial, skin anti-oxidant, skin anti-photoaging, skin anti-seborrheic, cell exchange and/or cell respiration activating of skin, skin conditioning, skin detoxifying, skin emollient, skin moisturizing, film forming on skin, skin healing-cicatrizing, skin immune-protecting, skin plumping, glossing, shading, plumping, and/or coloring of lips, skin revitalizing, skin energizing, skin re-sculpting, skin nourishing, skin smoothing, skin slimming, skin anti-irritating, and skin sanitizing.

Non-limiting applications of the oral care compositions include: tooth and/or mouth cleansing, providing denture adhesion, delivering and/or retaining actives to oral cavity, mouth washing, mouth refreshing, mouth rinsing, mouth gargling, providing oral hygiene, preventing, reducing, controlling, and/or removing tooth stain, preventing and/or controlling tooth decay, preventing and/or controlling tartar, tooth flossing, tooth whitening and/or bleaching, mouth treating, and tooth filling.

The polymers described herein also may be used alone or in combination with other ingredient(s) in pharmaceutical and/or nutritional compositions.

Non-limiting applications of the pharmaceutical and/or nutritional compositions include: providing anti-tack, binder, coating, disintegrating, dispersing, encapsulating, filling, film forming, lubricating, and solubilizing. Additional insight into how the polymers described herein find application in this art area may be found in the following publications by International Specialty Products: Health and nutrition product guide—Performance enhancing products (August/2008), Plasdone® povidones product overview (April/2010), Plasdone® K-12 and K-17 providones—Solubilizers for liquid softgel fill formulations (September/2010), Plasdone® K-29/32 povidone—High efficiency binder for wet granulation (April/2010), Plasdone® S-630 copovidone—Product Overview (April/2010), Polyplasdone® Ultra and Ultra-10 crospovidones—Product overview (September/2010), Polyplasdone® superdisintegrants—Product overview (July/2010), Polyplasdone® crospovidone—Superdisintegrants for orally disintegrating and chewable tablets (July/2010), Polyplasdone® crospovidone—Nonionic superdisintegrant for improved dissolution of cationic drugs (July/2009), Polyplasdone® crospovidone—The solution for poorly soluble drugs (July/2009), Polyplasdone® crospovidone—Novel pelletization aid for extrusion spheronization (July/2010), PVP-Iodine povidone iodine antiseptic agent (March/2004), and Pharmaceutical technical bulletin—PVP-Iodine for prophylaxis and treatment of bovine mastitis (December/2003). Each publication is hereby incorporated in its entirety by reference.

Any range in composition pH may be used. In embodiments wherein the composition is applied to keratinous material, the pH may range from about 2 to 12. pH may be adjusted to a desired value by means of adding one or more acidifying or alkalinizing agents that are well-known in the state of the art. For example, the composition can contain at least one alkalizing or acidifying agent in amounts from about 0.01% to about 30% based on the total weight of the composition.

Non-limiting examples of acidifying or acidic pH adjusting agents include organic acids, such as citric acid, acetic acid, carboxylic acids, α-hydroxyacids, β-hydroxyacids, α,β-hydroxyacids, γ-hydroxyacids, salicylic acid, tartaric acid, lactic acid, glycolic acid, natural fruit acids, and combinations thereof. In addition, inorganic acids, for example hydrochloric acid, nitric acid, sulfuric acid, sulfamic acid, phosphoric acid, and combinations thereof can be utilized.

Non-limiting examples of alkalizing or alkaline pH adjusting agents include ammonia, alkali metal hydroxides (such as sodium hydroxide and potassium hydroxide), ammonium hydroxide, alkanolamines (such as mono-, di- and triethanolamine), diisopropylamine, dodecylamine, diisopropanolamine, aminomethyl propanol, cocamine, oleamine, morpholine, triamylamine, triethylamine, tromethamine(2-amino-2-hydroxymethyl)-1,3-propanediol), and tetrakis(hydroxypropyl)ethylenediamine, hydroxyalkylamines and ethoxylated and/or propoxylated ethylenediamines, alkali metal salts of inorganic acids, such as sodium borate (borax), sodium phosphate, sodium pyrophosphate, and the like, and mixtures thereof.

Non-limiting examples of alkalizing agent can be chosen from ammonia, alkali carbonates, alkanolamines, like mono-, di- and triethanolamines, as well as their derivatives, sodium or potassium hydroxides and compounds of the following formula:

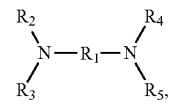

wherein $R_1$ is a propylene residue that may be optionally substituted with a hydroxyl group or a $C_1$-$C_4$ alkyl radical; $R_2$, $R_3$, $R_4$ and $R_5$ are identical or different and represent a hydrogen atom, a $C_1$-$C_4$ alkyl radical or $C_1$-$C_4$ hydroxyalkyl radical.

The composition also may comprise one or more buffers. Suitable buffering agents include but are not limited to alkali or alkali earth carbonates, phosphates, bicarbonates, citrates, borates, acetates, acid anhydrides, succinates and the like, such as sodium phosphate, citrate, borate, acetate, bicarbonate, and carbonate. The personal care compositions may be formulated in any of the product forms known to a person of ordinary skill in the art. Non-limiting product forms are described below.

Product Forms

Non-limiting hair care product forms include: shampoos, conditioners, aerosols, mousses, sprays, mists, gels, waxes, creams, lotions, glues, pomades, spritzes, solutions, oils, liquids, solids, W/O emulsions, O/W emulsions, suspensions, multiple emulsions, microemulsions, microencapsulated products, sticks, balms, tonics, pastes, reconstitutable products, nanoemulsions, solid lipid nanoparticles, liposomes, cubosomes, neosomes, putties, lacquers, serums, perms, volumizers, packs, flakes, 2-in-1 shampoo/conditioner products, and 3-in-1 shampoo/conditioner/styling products.

The compositions according to the invention may also take the form of after-shampoo compositions, to be rinsed off or not, for permanents, straightening, waving, dyeing, or bleaching, or the form of rinse compositions to be applied before or after dyeing, bleaching, permanents, straightening, relaxing, waving or even between the two stages of a permanent or straightening process.

Non-limiting sun care product forms include: solutions, liquids, creams, powders, lotions, gels, pastes, waxes, aerosols, sprays, mists, roll-ons, sticks, milks, emulsions, and wipes.

Non-limiting skin care product forms include: solutions, oils, lotions, creams, ointments, liquids, gels, solids, W/O emulsions, O/W emulsions, milks, suspensions, microemulsions, dispersions, microencapsulated products, sticks, balms, tonics, pastes, mists, reconstitutable products, peels, soaps, aerosols, mousses, waxes, glues, pomades, spritzes, putties, lacquers, serums, perms, powders, pencils, flakes, blush, highlighters, bronzers, concealers, and 2-way cake products.

The compositions of the invention may also take the form of skin-washing compositions, and particularly in the form of solutions or gels for the bath or shower, or of make-up removal products.

The six skin care product categories that follow next may be considered a subset of the skin and sun care products:

(1) Eye Care

Non-limiting eye care product forms include: mascaras, eye liners, eye shadows, curlers of eye lashes, eyebrow pencils, and eye pencils.

(2) Lip Care

Non-limiting lip care product forms include: lipsticks, lip balms, lip pencils, lip glosses, lip sprays, transparent lip bases, tinted lip moisturizers, and multi-functional color sticks that can also be used for cheeks and eyes.

(3) Nail Care

Non-limiting nail care product forms include: nail polishes, nail varnishes, enamels, nail varnish removers, home-manicure products such as cuticle softeners and nail strengtheners, and artificial nails.

(4) Face Care

Non-limiting face care product forms include: creams, lotions, solutions, oils, liquids, peels, scrubs, emulsions, suspensions, microemulsions, microencapsulated product, pastes, reconstitutable product, aerosols, mousses, gels, waxes, glues, pomades, spritzes, facial wet-wipes, putties, lacquers, serums, perms, powders, blush, highlighters, bronzers, masks, and concealers.

(5) Body Care

Non-limiting body care product forms include: foams, peels, masks, gels, sticks, aerosols, lotions, salts, oils, balls, liquids, powders, peels, pearls, bar soaps, liquid soaps, body washes, cleansers, scrubs, creams, flakes, other bath and shower products, shaving products, waxing products, and sanitizers.

(6) Foot Care

Non-limiting foot care product forms include: mousses, creams, lotions, powders, liquids, sprays, aerosols, gels, flakes, and scrubs.

Non-limiting oral care product forms include: toothpastes, adhesives, gums, gels, powders, creams, solutions, lotions, liquids, dispersions, suspensions, emulsions, tablets, capsules, rinses, flosses, aerosols, strips, films, pads, bandages, microencapsulated products, syrups, and lozenges.

Also contemplated are personal care compositions comprising polymer(s) described herein complexed with iodine. These compositions may be used in treating skin conditions, non-limiting examples of which include dermatitis, wounds, bacterial infections, burns, rashes, and herpes. These complexed compositions may be staining, substantially non-staining, or essentially non-staining.

Examples of related personal care compositions are disclosed in U.S. Pat. Nos. 5,599,800; 5,650,166; 5,916,549; and 6,812,192; U.S. patent application 2009/0317432; EP 556,660; 661,037; 661,038; 662,315; 676,194; 796,077; 970,682; 976383; 1,415,654; and 2,067,467; and WO 2005/032506; each of which is hereby incorporated in its entirety by reference.

It is also contemplated that the personal care compositions may be used in products for male and/or female personal grooming and/or toiletry such as: sanitary napkins, baby diapers, adult diapers, feminine products, products for incontinence, and other related products.

An array of additional personal care compositions, methods, and uses are contemplated. Disclosure of these compositions may be found in the following brochures by International Specialty Products, each of which is hereby incorporated in its entirety by reference: Plasdone® K-29/32, Advanced non-oxidative, non-abrasive teeth whitening in toothpastes, mouthwashes, and oral rinses (2010), Polymers for oral care, product and applications guide (2002), A formulation guide for excellent hair styling gels and lotions (April/2003), PVP (polyvinylpyrrolidone) (no date provided), and Textile chemicals, solutions for the most challenging product environment (no date provided).

Also contemplated are additional personal care compositions that may comprise the polymers described herein. Disclosures on such compositions may be found in the publications listed below, each of which is hereby incorporated in its entirety by reference: (1) Prototype Formulations—Personal Care Products (2009) from Xiameter, Dow Corning. (2) Sun care formulations under the category "Refreshing Sun", "Younger Sun", "Sun for Men", and "Sunny Glow" from Dow Corning. (3) Cosmetic Nanotechnology, Polymers and Colloids in Cosmetics, 2007, ACS Symposium Series. (4) Review Paper: Lipid nanoparticles (SLN, NLC) in cosmetic and pharmaceutical dermal products, International Journal of Pharmaceutics, Volume 366, 2009.

Optional: Additional Composition Ingredients

It is also contemplated that the personal care compositions optionally may contain one or more additional ingredients.

Further, it is contemplated that the composition ingredients may be formulated in a single container, or the ingredients may be formulated in-part in two or more distinct containers of the same or different type, the contents of which may require mixing prior to use.

Furthermore, it also is contemplated that the compositions may be prepared in the form of concentrates that may be diluted by a suitable substance(s) prior to use. The concentrate may, in turn, be present in any of the forms as described under 'Product Forms' for the personal care compositions of the invention.

A non-limiting list of classes of additional ingredients that may optionally be present in different types of personal care compositions is provided below: conditioning agents, antimicrobials, protectives (for example, antiradical agents), abrasives, UV absorbers, emulsifiers (including, but not limited to ethoxylated fatty acids, ethoxylated glyceryl esters, ethoxylated oils, ethoxylated sorbitan esters, fatty esters, PEG esters, polyglycerol esters), antiperspirants (including, but not limited to aluminium chlorohydrates, aluminium zirconium chlorohydrates), antioxidants, vitamins and/or provitamins, botanicals, fixatives, oxidizing agents, reducing agents, dyes, cleansing agents, anionic, cationic, nonionic, and/or amphoteric surfactants, thickeners and/or gelling agents, perfumes, flavors, and/or fragrances, pearlizing agents, stabilizers, pH adjusters, filters, antimicrobial agents, preservatives and/or disinfectants, associative polymers, oils of vegetable, mineral, and/or synthetic origin, polyols, silicones, colorants, bleaching agents, highlighting agents, propellants (including, but not limited to hydrocarbons, dimethyl ether, fluorocarbons), styling polymers, benefit agents, skin lighteners (including, but not limited to arbutin and kojic acids), tanning agents (including, but not limited to dihydroxyacetone), solvents and/or cosolvents, diluents, essential oils, sequestrants and/or chelators, carriers, and natural extracts and/or natural products.

The amount of each ingredient in the composition varies depending on the type of composition, the function and/or physicochemical property of the ingredient, and the amount of other co-ingredients. The precise amount of each ingredient may be easily determined by any person skilled in the related arts.

It may be desirable to include one or more ingredients described in the prior art disclosures IPCOM000186541D, IPCOM000128968D, and IPCOM000109682D on www.ip.com, the contents of each of these disclosures are hereby incorporated in their entirety by reference.

Further reference to formulary co-ingredients and product forms include the disclosures in US 2010/0183532, paragraphs [0096]-[0162], and WO 2010/105050, paragraphs [0053]-[0069], the contents of which are hereby incorporated in their entirety by reference.

Non-limiting examples of structurants that may be used in the hair care compositions according to the invention include dextrin palmitate, trihydroxystearin, hydroxy stearic acid, hydrophilic or hydrophobic silica, hydrophobically modified clay selected from the group consisting of stearalkonium hectorite, quaternium-18 bentonite, quaternium-18 hectorite, disteardimonium hectorite, derivatives thereof, and mixtures thereof.

Any known conditioning agent may be used in the personal care compositions of the invention. An extensive discussion on conditioning agents may be found in the book Conditioning Agents for Skin and Hair, Cosmetic Science and Technology Series, Volume 21, 1999, Marcel Dekker Publishers. The contents of the book are hereby incorporated in its entirety by reference.

Conditioning agents may be chosen from synthetic oils, mineral oils, vegetable oils, fluorinated or perfluorinated oils, natural or synthetic waxes, silicones, cationic polymers, proteins and hydrolyzed proteins, cationic surfactants, ceramide type compounds, fatty amines, fatty acids and their derivatives, as well as mixtures of these different types of compounds.

Non-limiting examples of suitable synthetic oils include: polyolefins, e.g., poly-α-olefins, such as polybutenes, polyisobutenes, polydecenes, and blends thereof. The polyolefins may be hydrogenated.

Non-limiting examples of suitable mineral oils include hexadecane and oil of paraffin.

Non-limiting examples of suitable animal and vegetable oils include: sunflower oil, corn oil, soy oil, avocado oil, jojoba oil, squash oil, raisin seed oil, sesame seed oil, walnut oil, fish oil, glycerol tricaprocaprylate, purcellin oil, liquid jojoba, and blends thereof. Also suitable are natural oils such as oils of eucalyptus, lavender, vetiver, litsea cubeba, lemon, sandalwood, rosemary, chamomile, savory, nutmeg, cinnamon, hyssop, caraway, orange, geranium, cade, bergamot, and blends thereof.

The conditioning agent may be fluorinated or perfluorinated oil. The fluoridated oils may also be fluorocarbons such as fluoramines, e.g., perfluorotributylamine, fluoridated hydrocarbons such as perfluorodecahydronaphthalene, fluoroesters, fluoroethers, and blends thereof.

Non-limiting examples of suitable natural and synthetic waxes include: carnauba wax, candelila wax, alfa wax, paraffin wax, ozokerite wax, vegetable waxes such as olive wax, rice wax, hydrogenated jojoba wax, absolute flower waxes such as black currant flower wax, animal waxes such as bees wax, modified bees wax (cerabellina), marine waxes and polyolefin waxes such as polyethylene wax, and blends thereof.

The conditioning agent may be any silicone known by those skilled in the art. Silicones include polyorganosiloxanes that are insoluble in the composition. The silicones may be present in the form of oils, waxes, resins, or gums. They may be volatile or non-volatile.

Non-limiting examples of suitable silicones include: polyalkyl siloxanes, polyaryl siloxanes, polyalkyl aryl siloxanes, silicone gums and resins, polyorgano siloxanes modified by organofunctional groups, and blends thereof.

Suitable polyalkyl siloxanes include polydimethyl siloxanes with terminal trimethyl silyl groups or terminal dimethyl silanol groups (dimethiconol) and polyalkyl($C_1$-$C_{20}$) siloxanes. Suitable polyalkyl aryl siloxanes include polydimethyl methyl phenyl siloxanes and polydimethyl diphenyl siloxanes. The siloxanes can have a linear or branched structure.

Suitable silicone gums include polydiorganosiloxanes, such as those having a number-average molecular weight between 200,000 Da and 1,000,000 Da used alone or mixed with a solvent.

Non-limiting examples of suitable silicone gums include: polymethyl siloxane, polydimethyl siloxane/methyl vinyl siloxane gums, polydimethyl siloxane/diphenyl siloxane, polydimethyl siloxane/phenyl methyl siloxane, polydimethyl siloxane/diphenyl siloxane/methyl vinyl siloxane, and blends thereof.

Non-limiting examples of suitable silicone resins include silicones with a dimethyl/trimethyl siloxane structure and resins of the trimethyl siloxysilicate type.

The organo-modified silicones suitable for use in the invention include silicones such as those previously defined and containing one or more organofunctional groups attached by means of a hydrocarbon radical, and grafted silicone polymers. The organo-modified silicones may be one from the amino functional silicone family.

The silicones may be used in the form of emulsions, nano-emulsions, or microemulsions.

The cationic polymers that may be used as conditioning agents according to the invention generally have a molecular weight (average number) from about 500 Da to about 5,000,000 Da, particularly from about 1,000 Da to about 3,000,000 Da. The expression "cationic polymer" as used herein indicates any polymer having at least one cationic group.

The cationic polymers may be chosen from among polymers containing primary, secondary, tertiary amine, and/or quaternary ammonium groups that may form part of the main polymer backbone and/or side chain(s).

Non-limiting examples of suitable cationic polymers include polyamines, polyaminoamides, and quaternary polyammonium classes of polymers, such as:

(1) homopolymers and copolymers derived from acrylic or methacrylic esters or amides. The copolymers may contain one or more units derived from acrylamides, methacrylamides, diacetone acrylamides, acrylic or methacrylic acids or their esters, vinyllactams such as vinyl pyrrolidone or vinyl caprolactam, and vinyl esters. Non-limiting, specific examples include: copolymers of acrylamide and dimethyl amino ethyl methacrylate quaternized with dimethyl sulfate or with an alkyl halide; copolymers of acrylamide and methacryloyl oxyethyl trimethyl ammonium chloride; the copolymer of acrylamide and methacryloyl oxyethyl trimethyl ammonium methosulfate; copolymers of vinyl pyrrolidone and dialkylaminoalkyl acrylate or methacrylate, optionally quaternized, such as the products sold under the name Gafquat® by International Specialty Products; terpolymers of dimethyl amino ethyl methacrylate, vinyl caprolactam, and vinyl pyrrolidone such as the product sold under the name Gaffix® VC 713 by International Specialty Products; the vinyl pyrrolidone/methacrylamidopropyl dimethylamine copolymer, marketed under the name Styleze® CC 10 by International Specialty Products; and the vinyl pyrrolidone/quaternized dimethyl amino propyl methacrylamide copolymers such as the product sold under the name Gafquat® HS 100 by International Specialty Products (Wayne, N.J.).

(2) derivatives of cellulose ethers containing quaternary ammonium groups, such as hydroxy ethyl cellulose quaternary ammonium that has reacted with an epoxide substituted by a trimethyl ammonium group.

(3) derivatives of cationic cellulose such as cellulose copolymers or derivatives of cellulose grafted with a hydrosoluble quaternary ammonium monomer, as described in U.S. Pat. No. 4,131,576, such as hydroxy alkyl cellulose, and hydroxymethyl-, hydroxyethyl- or hydroxypropyl-cellulose grafted with a salt of methacryloyl ethyl trimethyl ammonium, methacrylamidopropyl trimethyl ammonium, or dimethyl diallyl ammonium.

(4) cationic polysaccharides such as described in U.S. Pat. Nos. 3,589,578 and 4,031,307, guar gums containing cationic trialkyl ammonium groups, and guar gums modified by a salt, e.g., chloride of 2,3-epoxy propyl trimethyl ammonium.

(5) polymers composed of piperazinyl units and alkylene or hydroxy alkylene divalent radicals with straight or branched chains, possibly interrupted by atoms of oxygen, sulfur, nitrogen, or by aromatic or heterocyclic cycles, as well as the products of the oxidation and/or quaternization of such polymers.

(6) water-soluble polyamino amides prepared by polycondensation of an acid compound with a polyamine. These polyamino amides may be reticulated.

(7) derivatives of polyamino amides resulting from the condensation of polyalkylene polyamines with polycarboxylic acids followed by alkylation by bi-functional agents.

(8) polymers obtained by reaction of a polyalkylene polyamine containing two primary amine groups and at least one secondary amine group with a dioxycarboxylic acid chosen from among diglycolic acid and saturated dicarboxylic aliphatic acids having 3 to 8 atoms of carbon. Such polymers include those described in U.S. Pat. Nos. 3,227,615 and 2,961,347.

(9) cyclopolymers of alkyl diallyl amine or dialkyl diallyl ammonium such as the homopolymer of dimethyl diallyl ammonium chloride and copolymers of diallyl dimethyl ammonium chloride and acrylamide.

(10) quaternary diammonium polymers such as hexadimethrine chloride.

(11) quaternary polyammonium polymers, including, for example, Mirapol® A 15, Mirapol® AD1, Mirapol® AZ1, and Mirapol® 175 products sold by Miranol.

(12) quaternary polymers of vinyl pyrrolidone and vinyl imidazole such as the products sold under the names Luviquat® FC 905, FC 550, and FC 370 by BASF Corporation.

(13) quaternary polyamines.

(14) reticulated polymers known in the art.

Other cationic polymers that may be used include cationic proteins or hydrolyzed cationic proteins, polyalkyleneimines such as polyethyleneimines, polymers containing vinyl pyridine or vinyl pyridinium units, condensates of polyamines and epichlorhydrins, quaternary polyurethanes, and derivatives of chitin.

The conditioning agent may comprise a protein or hydrolyzed cationic or non-cationic protein. Non-limiting examples of suitable compounds include: hydrolyzed collagens having triethyl ammonium groups, hydrolyzed collagens having trimethyl ammonium and trimethyl stearyl ammonium chloride groups, hydrolyzed animal proteins having trimethyl benzyl ammonium groups (benzyltrimonium hydrolyzed animal protein), hydrolyzed proteins having groups of quaternary ammonium on the polypeptide chain, including at least one $C_1$-$C_{18}$ alkyl, and blends thereof.

Non-limiting examples of suitable hydrolyzed cationic proteins include: Croquat® L, in which the quaternary ammonium groups include a $C_{12}$ alkyl group, Croquat® M, in which the quaternary ammonium groups include $C_{10}$-$C_{18}$ alkyl groups, Croquat® S in which the quaternary ammonium groups include a $C_{18}$ alkyl group, Crotein® Q in which the quaternary ammonium groups include at least one $C_1$-$C_{18}$ alkyl group, and blends thereof. These products are sold by Croda.

The conditioning agent may also comprise quaternized vegetable protein(s) such as wheat, corn, or soy proteins, non-limiting examples of which include: cocodimonium hydrolyzed wheat protein, laurdimonium hydrolyzed wheat protein, steardimonium hydrolyzed wheat protein, 2-N-stearoylaminooctadecane-1,3-diol, 2-N-behenoylaminooctadecane-1,3-diol, 2-N-[2-hydroxy-palmitoyl]aminooctadecane-1,3-diol, 2-N-stearoylaminooctadecane-1,3,4-triol, N-stearoylphytosphingosine, 2-N-palmitoylaminohexadecane-1,3-diol, bis-(N-hydroxy ethyl N-cetyl)malonamide, N-(2-hydroxyethyl)-N-(3-cetoxyl-2-hydroxypropyl)amide of cetylic acid, N-docosanoyl-N-methyl-D-glucamine, and blends thereof.

The conditioning agent may also comprise a cationic surfactant such as a salt of a primary, secondary, or tertiary fatty amine, optionally polyoxyalkylenated, a quaternary ammonium salt, a derivative of imadazoline, or an amine oxide. Conditioning agents may also be selected from the group consisting of: mono-, di-, and tri-alkyl amines, and quaternary ammonium compounds with a counterion such as a chloride, a methosulfate, a tosylate, etc. Non-limiting examples of suitable amines include: cetrimonium chloride, dicetyldimonium chloride, behentrimonium methosulfate, and blends thereof.

The conditioning agent may comprise a fatty amine. Non-limiting examples of suitable fatty amines include: dodecyl amines, cetyl amines, stearyl amines such as stearamidopropyl dimethylamine, and blends thereof.

The conditioning agent may comprise a fatty acid or derivative(s) thereof. Non-limiting examples of suitable fatty acids include: myristic acid, palmitic acid, stearic acid, behenic acid, oleic acid, linoleic acid, isostearic acid, and blends thereof. The derivatives of fatty acids include carboxylic ester acids including mono-, di-, tri- and tetra-carboxylic acids esters, amides, anhydrides, esteramides, imides, and mixtures of these functional groups.

Also suitable as conditioning agents are the following commercial products:

(1) Aquacat™ Clear Cationic Solution (INCI Name: guar hydroxypropyltrimonium Chloride), N-Hance™ SP-100 (INCI Name: acrylamidopropyl trimonium chloride/acrylamide copolymer), and N-Hance™ cationic guar (INCI Name: guar hydroxypropyltrimonium chloride) from Ashland Inc.

(2) Salcare® from BASF Corp.

(3) Softcat™ Polymers from The Dow Chemical Company.

(4) Jaguar® C500, Polycare® Boost, Mackconditioner™ Brite, and Mackine® 301 from Rhodia.

(5) Stepanquat® ML, Stepanquat® GA-90, Ninol®, and Ammonyx® from Stepan Company.

(6) Conditioneze 7 and Conditioneze NT-20 from International Specialty Products (Wayne, N.J.).

Of course, mixtures of two or more conditioning agents may be used.

The conditioning agent(s) may be present in an amount from about 0.001% to about 20%, particularly from about 0.01% to about 10%, and even more particularly from about 0.1% to about 3% by weight of the composition.

Personal care compositions may optionally comprise antimicrobial agent(s).

Non-limiting examples of suitable water insoluble, non-cationic antimicrobial agents include: halogenated diphenyl ethers, phenolic compounds including phenol and its homologs, mono and poly-alkyl and aromatic halophenols, resorcinol and its derivatives, bisphenolic compounds and halogenated salicylanilides, benzoic esters, halogenated carbanilides, and blends thereof.

Non-limiting examples of suitable water soluble antimicrobial agents include: quaternary ammonium salts, bisbiquanide salts, triclosan monophosphate, and blends thereof.

The quaternary ammonium agents include those in which one or two of the substituents on the quaternary nitrogen has a carbon chain length (typically alkyl group) from about 8 to about 20, typically from about 10 to about 18 carbon atoms, while the remaining substituents (typically alkyl or benzyl group) have a lower number of carbon atoms, such as from about 1 to about 7 carbon atoms, typically methyl or ethyl groups.

Non-limiting examples of suitable quaternary ammonium antibacterial agents include: Dodecyl trimethyl ammonium bromide, tetradecylpyridinium chloride, domiphen bromide, N-tetradecyl-4-ethyl pyridinium chloride, dodecyl dimethyl (2-phenoxyethyl)ammonium bromide, benzyl dimethylstearyl ammonium chloride, cetyl pyridinium chloride, quaternized 5-amino-1,3-bis(2-ethyl-hexyl)-5-methyl hexahydropyrimidine, benzalkonium chloride, benzethonium chloride, methyl benzethonium chloride, and blends thereof.

Other antimicrobial compounds are bis[4-(R-amino)-1-pyridinium]alkanes as disclosed in U.S. Pat. No. 4,206,215. Other antimicrobials such as copper salts, zinc salts and/or stannous salts may also be included. Also useful are enzymes, including endoglycosidase, papain, dextranase, mutanase, and blends thereof. Such antimicrobial agents are disclosed in U.S. Pat. Nos. 2,946,725 and 4,051,234. The antimicrobial agents may also comprise chlorhexidine, triclosan, and flavor oils such as thymol. Triclosan and other agents are disclosed in U.S. Pat. Nos. 5,015,466 and 4,894,220.

In particular embodiments, one or more preservatives may be included.

Non-limiting examples of suitable preservatives include: benzoic acid, sorbic acid, dehydroacetic acid, diazolidinyl ureas, imidazolidinyl ureas, salicylic acid, piroctone olamine, DMDM hydantoin, IPBC (iodopropynyl butylcarbamate), triclosan, bronopol, formaldehyde, isothiazolinones, nitrates/nitrites, parabens, phenoxyethanol, potassium sorbate, sodium benzoate, sulphites, sulphur dioxide, and blends thereof.

In particular embodiments, preservative boosters/solvents may be incorporated, non-limiting examples of which include: caprylyl glycol, hexylene glycol, pentylene glycol, ethylhexylglycerin, caprylhydroxamic acid, caprylohydroxamic acid, glyceryl caprylate, and blends thereof.

Polysaccharides, such as gum Arabic, may be included as well.

Personal care compositions may comprise liquid or liquid-like carrier(s) that help to distribute, disperse, and/or dissolve the ingredients.

Non-limiting examples of suitable liquid carriers include: water, alcohols, oils, esters, and blends thereof.

The compositions of the invention may also be in the form of aqueous or hydro-alcoholic solutions.

The physiological and cosmetically acceptable medium may consist exclusively of water, a cosmetically acceptable solvent, or a blend of water and a cosmetically acceptable solvent, such as a lower alcohol composed of $C_1$ to $C_4$, such as ethanol, isopropanol, t-butanol, n-butanol, alkylene glycols such as propylene glycol, and glycol ethers.

In one of the embodiment, the compositions of the invention may be anhydrous.

Typically, sun care compositions may also comprise one or more UV actives, which include organic and inorganic materials that scatter, absorb, and/or reflect radiation having a wavelength from about 100 nm to about 400 nm.

In one particular embodiment, the sun care compositions protect against UV-A, UV-B, and/or UV-C radiation.

UV-A radiation, from about 320 nm to about 400 nm, has the longest wavelengths within the UV spectrum, and consequently is the least energetic. UV-A radiation includes UV-A1 (from about 340 nm to about 400 nm) and UV-A2 (from about 320 nm to about 340 nm). UV-B radiation has shorter wavelengths, from about 290 nm to about 320 nm. UV-C radiation has the shortest wavelengths from about 200 nm to about 290 nm.

In another embodiment, the sun care compositions may not contain UV actives, and may be regarded as tanning oils or tan promoters.

Sun care compositions may be formulated, for example, for application to the lips, hair, face, cheeks, neck, area around the eyes, full hands, and body area. Self-tanning compositions, which are products that color skin without requiring full sun exposure, also fit under the sun care umbrella.

Suitable UV absorber(s) that may be included in the personal care compositions most likely will depend on local regulations. As the rules governing the names and usage levels evolve over time, it is impossible to include every UV absorber that may be used with the invention.

Non-limiting examples of suitable UV absorbers include: octyl salicylate; pentyl dimethyl PABA; octyl dimethyl PABA; benzophenone-1; benzophenone-6; 2-(2H-benzotriazole-2-yl)-4,6-di-tert-pentylphenol; ethyl-2-cyano-3,3-diphenylacrylate; homomethyl salicylate; bis-ethylhexyloxyphenol methoxyphenyl triazine; methyl-(1,2,2,6,6-pentamethyl-4-piperidyl)-sebacate; 2-(2H-benzotriazole-2-yl)-4-methylphenol; diethylhexyl butamido triazone; amyl dimethyl PABA; 4,6-bis(octylthiomethyl)-o-cresol; CAS number 65447-77-0; red petroleum; ethylhexyl triazone; octocrylene; isoamyl-p-methoxycinnamate; drometrizole; titanium dioxide; 2,4-di-tert-butyl-6-(5-chloro-2H-benzotriazole-2-yl)-phenol; 2-hydroxy-4-octyloxybenzophenone; benzophenone-2; diisopropyl methylcinnamate; PEG-PABA; 2-(1,1-dimethylethyl)-6-[[3-(1,1-demethylethyl)-2-hydroxy-5-methylphenyl]methyl-4-methylphenyl acrylate; drometrizole trisiloxane; menthyl anthranilate; butyl methoxydibenzoylmethane; 2-ethoxyethyl p-methoxycinnamate; benzylidene camphor sulfonic acid; dimethoxyphenyl-[1-(3,4)]-4,4-dimethyl 1,3-pentanedione; zinc oxide; N,N'-hexane-1,6-diylbis[3-(3,5-di-tert-butyl-4-hydroxyphenylpropionamide)]; pentaerythritol tetrakis[3-(3,5-di-tert-butyl-4-hydroxyphenyl)propionate]; 2,6-di-tert-butyl-4-[4, 6-bis(octylthio)-1,3,5-triazin-2-ylamino]phenol; 2-(2H-benzotriazole-2-yl)-4,6-bis(1-methyl-1-phenylethyl)phenol; trolamine salicylate; diethylanolamine p-methoxycinnamate; polysilicone-15; CAS number 152261-33-1; 4-methylbenzylidene camphor; bisoctrizole; N-phenyl-benzenamine; reaction products with 2,4,4-trimethylpentene; sulisobenzone; (2-ethylhexyl)-2-cyano-3,3-diphenylacrylate; digalloyl trioleate; polyacrylamido methylbenzylidene camphor; glyceryl ethylhexanoate dimethoxycinnamate; 1,3-bis-[(2'-cyano-3',3'-diphenylacryloyl)oxy]-2,2-bis-{[(2'-cyano-bis-(2,2,6,6-tetramethyl-4-piperidyl)-sebacate; benzophenone-5; 1,3,5-tris(3,5-di-tert-butyl-4-hydroxybenzyl)-1,3,5-triazine-2,4,6(1H,3H,5H)-trione; hexamethylendiamine; benzophenone-8; ethyl-4-bis(hydroxypropyl)aminobenzoate; 6-tert-butyl-2-(5-chloro-2H-benzotriazole-2-yl)-4-methylphenol; p-aminobenzoic acid; 3,3',3'',5,5',5''-hexa-tert-butyl-α-α'-α''-(mesitylene-2,4,6-triyl)tri-p-cresol; lawsone with dihydroxyacetone; benzophenone-9; benzophenone-4; ethylhexyl dimethoxy benzylidene dioxoimidazoline propionate; N,N'-bisformyl-N,N'-bis-(2,2,6,6-tetramethyl-4-piperidinyl)-; 3-benzylidene camphor; terephthalylidene dicamphor sulfonic acid; camphor benzalkonium methosulfate; bisdisulizole disodium; etocrylene; ferulic acid; 2-(2H-benzotriazole-2-yl)-4-(1,1,3,3-tetramethylbutyl)-phenol; 4,6-bis(dodecylthiomethyl)-o-cresol; β-2-glucopyranoxy propyl hydroxy benzophenone; phenylbenzimidazole sulfonic acid; benzophenone-3; diethylamine hydroxybenzoyl hexylbenzoate; 3',3'-diphenylacryloyl)oxy]methyl}-propane; ethylhexyl p-methoxycinnamate, and blends thereof.

Personal care compositions may comprise antioxidant(s) and/or antiradical protecting agent(s).

Non-limiting examples of suitable antioxidants and/or antiradical protecting agents include: BHA (tert-butyl-4-hydroxy anisole), BHT (2,6-di-tert-butyl-p-cresol), TBHQ (tert-butyl hydroquinone), polyphenols such as proanthocyanodic oligomers, flavonoids, hindered amines such as tetra amino piperidine, erythorbic acid, polyamines such as spermine, cysteine, glutathione, superoxide dismutase, lactoferrin, and blends thereof.

Personal care compositions may comprise vitamin(s), provitamin(s), and/or mineral(s).

Non-limiting examples of suitable vitamins include: ascorbic acid (vitamin C), vitamin E, vitamin E acetate, vitamin E phosphate, B vitamins such as B3 and B5, niacin, vitamin A, derivatives thereof, and blends thereof.

Non-limiting examples of suitable provitamins include: panthenol, retinol, and blends thereof.

Non-limiting examples of suitable minerals include: talc, clay, calcium carbonate, silica, kaolin, mica, and blends thereof. Further examples of minerals that may be used in the personal care compositions may be found in a brochure titled Minerals for Personal Care from Imerys Performance Minerals, the disclosure of which is hereby incorporated in its entirety by reference.

Personal care compositions may comprise one or more surfactants. Surfactants serve in solubilizing, dispersing, emulsifying and/or reducing the interfacial tension. Surfactants may be chosen from anionic, nonionic, amphoteric, zwitterionic, or cationic surfactants, or blends thereof.

Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate (SLS) and sodium coconut monoglyceride sulfonates are non-limiting examples of anionic surfactants of this type.

Non-limiting examples of suitable anionic surfactants include: sarcosinates, taurates, isethionates, sodium lauryl sulfoacetate, sodium laureth carboxylate, and sodium dodecyl benzenesulfonate. Also suitable are alkali metal or ammonium salts of surfactants such as the sodium and potassium salts of the following: lauroyl sarcosinate, myristoyl sarcosinate, palmitoyl sarcosinate, stearoyl sarcosinate, and oleoyl sarcosinate.

Non-limiting examples of suitable cationic surfactants include: derivatives of aliphatic quaternary ammonium compounds having at least one long alkyl chain containing from about 8 to about 18 carbon atoms, such as, lauryl trimethylammonium chloride, cetyl pyridinium chloride, cetyl trimethylammonium bromide, di-isobutylphenoxyethyl-dimethylbenzylammonium chloride, coconut alkyltrimethylammonium nitrite, cetyl pyridinium fluoride, and blends thereof. Further suitable are quaternary ammonium fluorides having detergent properties such as compounds described in U.S. Pat. No. 3,535,421. Certain cationic surfactants may act as germicides in the compositions disclosed herein.

Nonionic surfactants useful herein include compounds produced by the condensation of alkylene oxide groups (hydrophilic in nature) with an organic hydrophobic compound which may be aliphatic or alkylaromatic in nature.

Non-limiting examples of suitable nonionic surfactants include: poloxamers (sold under the trade name Pluronic® by BASF Corporation), polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and blends thereof.

Non-limiting examples of suitable zwitterionic surfactants include betaines and derivatives of aliphatic quaternary ammonium compounds in which the aliphatic radicals can be straight chain or branched, and which contain an anionic water-solubilizing group, e.g., carboxy, sulfonate, sulfate, phosphate, or phosphonate.

Non-limiting examples of suitable betaines include: decyl betaine or 2-(N-decyl-N,N-dimethylammonio)acetate, coco betaine or 2-(N-coco-N,N-dimethyl ammonio)acetate, myristyl betaine, palmityl betaine, lauryl betaine, cetyl betaine, stearyl betaine, and blends thereof. The amidobetaines are exemplified by cocoamidoethyl betaine, cocoamidopropyl betaine, lauramidopropyl betaine, and the like. The betaines of choice include cocoamidopropyl betaines such as lauramidopropyl betaine. Suitable betaine surfactants are disclosed in U.S. Pat. No. 5,180,577.

Other surfactants such as fluorinated surfactants may also be incorporated within the compositions of the invention.

Also suitable as surfactants are the following commercial products:

(1) Alkanolamides, under the trade names Amidex™ and Schercomid™; amido-amines, under the trade names Katemul™ and Schercodine™; amine oxides, under the trade names Chemoxide™ and Schercamox™; amphoterics, under the trade names Chembetaine™, Schercotaine™ and Schercoteric™; imidazolines, under the trade name Schercozoline™; pearlizing agents, under the trade name Quickpearl™; performance concentrates, under the trade names Sulfochem™ and Chemoryl™; soaps (potassium cocoate and potassium soyate); specialty ethoxylates, under the trade name Chemonic™; specialty quats under the trade names Quatrex™ and Schercoquat™; sulfates, under the trade name Sulfochem™; and sulfosuccinates, under the trade name Chemccinate™ from Lubrizol.

(2) Avaniel, Cremaphore®, Jordapan®, and Pluracare® from BASF Corp.

(3) Miracare® SLB, Mackam® Bab, Mackanate® Ultra SI, Miranol® Ultra, and Miracare® Plaisant from Rhodia.

(4) Stepan® Pearl 2, Stepan® Pearl 4, Stepan® Pearl Series, Neobee® M-20, Stepan® PTC, Amphosol® 2CSF, Steol®, Stepan-Mild® GCC, Stepan® SLL-FB, Stepanol® AM, Stepanol® PB, Alpha-Step® BSS-45, Bio-Terge® 804, Stepan-Mild® L3, Stepan® SLL-FB, Stepan® SSL-CG, and Stepanol® CFAS-70 from Stepan Company.

Also suitable as surfactants are those described in the book Surfactants in Personal Care Products and Decorative Cosmetics, Third Edition, 2006, CRC Press. The disclosure is incorporated hereby in its entirety by reference.

Personal care compositions may be also be formulated as detergent compositions, such as shampoos, bath gels, and bubble baths. Such compositions comprise water as a liquid carrier. The surfactant or surfactants that form the washing base may be chosen alone or in blends, from known anionic, amphoteric, zwitterionic and/or non-ionic surfactants. The quantity and quality of the washing base must be sufficient to impart a satisfactory foaming and/or detergent value to the final composition. The washing base may be present in an amount from about 4% to about 50% by weight, particularly from about 6% to about 35% by weight, and more particularly from about 8% to about 25% by weight of the final composition.

Personal care compositions may comprise one or more thickener(s) and/or viscosifier(s).

Non-limiting examples of suitable thickeners and/or viscosifiers include: Acetamide MEA; acrylamide/ethalkonium chloride acrylate copolymer; acrylamide/ethyltrimonium chloride acrylate/ethalkonium chloride acrylate copolymer; acrylamides copolymer; acrylamide/sodium acrylate copolymer; acrylamide/sodium acryloyldimethyltaurate copolymer; acrylates/acetoacetoxyethyl methacrylate copolymer; acrylates/beheneth-25 methacrylate copolymer; acrylates/$C_{10}$-$C_{30}$ alkyl acrylate crosspolymer; acrylates/ceteth-20 itaconate copolymer; acrylates/ceteth-20 methacrylate copolymer; acrylates/laureth-25 methacrylate copolymer; acrylates/palmeth-25 acrylate copolymer; acrylates/palmeth-25 itaconate copolymer; acrylates/steareth-50 acrylate copolymer; acrylates/steareth-20 itaconate copolymer; acrylates/steareth-20 methacrylate copolymer; acrylates/stearyl methacrylate copolymer; acrylates/vinyl isodecanoate crosspolymer; acrylic acid/acrylonitrogens copolymer; adipic acid/methyl DEA crosspolymer; agar; agarose; alcaligenes polysaccharides; algin; alginic acid; almondamide DEA; almondamidopropyl betaine; aluminum/magnesium hydroxide stearate; ammonium acrylates/acrylonitrogens copolymer; ammonium acrylates copolymer; ammonium acryloyldimethyltaurate/vinyl formamide copolymer; ammonium acryloyldimethyltaurate/VP copolymer; ammonium alginate; ammonium chloride; ammonium polyacryloyldimethyl taurate; ammonium sulfate; amylopectin; apricotamide DEA; apricotamidopropyl betaine; arachidyl alcohol; arachidyl glycol; *arachis hypogaea* (peanut) flour; ascorbyl methylsilanol pectinate; *astragalus* gummifer gum; attapulgite; *avena sativa* (oat) kernel flour; avocadamide DEA; avocadamidopropyl betaine; azelamide MEA; babassuamide DEA; babassuamide MEA; babassuamidopropyl betaine; behenamide DEA; behenamide MEA; behenamidopropyl betaine; behenyl betaine; bentonite; butoxy chitosan; caesalpinia spinosa gum; calcium alginate; calcium carboxymethyl cellulose; calcium carrageenan; calcium chloride; calcium potassium carbomer; calcium starch octenylsuccinate; C20-40 alkyl stearate; canolamidopropyl betaine; capramide DEA; capryl/capramidopropyl betaine; carbomer; carboxybutyl chitosan; carboxymethyl cellulose acetate butyrate; carboxymethyl chitin; carboxymethyl chitosan; carboxymethyl dextran; carboxymethyl hydroxyethylcellulose; carboxymethyl hydroxypropyl guar; carnitine; cellulose acetate propionate carboxylate; cellulose gum; ceratonia siliqua gum; cetearyl alcohol; cetyl alcohol; cetyl babassuate; cetyl betaine; cetyl glycol; cetyl hydroxyethylcellulose; chimyl alcohol; cholesterol/HDI/pullulan copolymer; cholesteryl hexyl dicarbamate pullulan; citrus aurantium dulcis (orange) peel extract; cocamide DEA; cocamide MEA; cocamide MIPA; cocamidoethyl betaine; cocamidopropyl betaine; cocamidopropyl hydroxysultaine; cocobetaine; coco-hydroxysultaine; coconut alcohol; coco/oleamidopropyl betaine; coco-Sultaine; cocoyl sarcosinamide DEA; cornamide/cocamide DEA; cornamide DEA; croscarmellose; crosslinked *bacillus*/glucose/sodium glutamate ferment; *cyamopsis tetragonoloba* (guar) gum; decyl alcohol; decyl betaine; dehydroxanthan gum; dextrin; dibenzylidene sorbitol; diethanolaminooleamide DEA; diglycol/CHDM/isophthalates/SIP copolymer; dihydroabietyl behenate; dihydrogenated tallow benzylmonium hectorite; dihydroxyaluminum aminoacetate; dimethicone/PEG-10 crosspolymer; dimethicone/PEG-15 crosspolymer; dimethicone propyl PG-betaine; dimethylacrylamide/acrylic acid/polystyrene ethyl methacrylate copolymer; dimethylacrylamide/sodium acryloyldimethyltaurate crosspolymer; disteareth-100 IPDI; DMAPA acrylates/acrylic acid/acrylonitrogens copolymer; erucamidopropyl hydroxysultaine; ethylene/sodium acrylate copolymer; gelatin; gellan gum; glyceryl alginate; glycine soja (soybean) flour; guar hydroxypropyltrimonium chloride; hectorite; hyaluronic acid; hydrated silica; hydrogenated potato starch; hydrogenated tallow; hydrogenated tallowamide DEA; hydrogenated tallow betaine; hydroxybutyl methylcellulose; hydroxyethyl acrylate/sodium acryloyldimethyl taurate copolymer; hydroxyethylcellulose; hydroxyethyl chitosan; hydroxyethyl ethylcellulose; hydroxyethyl stearamide-MIPA; hydroxylauryl/hydroxymyristyl betaine; hydroxypropylcellulose; hydroxypropyl chitosan; hydroxypropyl ethylenediamine carbomer; hydroxypropyl guar; hydroxypropyl methylcellulose; hydroxypropyl methylcellulose stearoxy ether; hydroxypropyl starch; hydroxypropyl starch phosphate; hydroxypropyl xanthan gum; hydroxystearamide MEA; isobutylene/sodium maleate copolymer; isostearamide DEA; isostearamide MEA; isostearamide mIPA; isostearamidopropyl betaine; lactamide MEA; lanolinamide DEA; lauramide DEA; lauramide MEA; lauramide MIPA; lauramide/myristamide DEA; lauramidopropyl betaine; lauramidopropyl hydroxysultaine; laurimino bispropanediol; lauryl alcohol; lauryl betaine; lauryl hydroxysultaine; lauryl/myristyl glycol hydroxypropyl ether; lauryl sultaine; lecithinamide DEA; linoleamide DEA; linoleamide MEA; linoleamide MIPA; lithium magnesium silicate; lithium magnesium sodium silicate; macrocystis pyrifera (kelp); magnesium alginate; magnesium/aluminum/hydroxide/carbonate; magnesium aluminum silicate; magnesium silicate; magnesium trisilicate; methoxy PEG-22/dodecyl glycol copolymer; methylcellulose; methyl ethylcellulose; methyl hydroxyethylcellulose; microcrystalline cellulose; milkamidopropyl betaine; minkamide DEA; minkamidopropyl betaine; MIPA-myristate; montmorillonite; Moroccan lava clay; myristamide DEA; myristamide MEA; myristamide MIPA; myristamidopropyl betaine; myristamidopropyl hydroxysultaine; myristyl alcohol; myristyl betaine; natto gum; nonoxynyl hydroxyethylcellulose; oatamide MEA; oatamidopropyl betaine; octacosanyl glycol isostearate; octadecene/MA copolymer; oleamide DEA; oleamide MEA; oleamide MIPA; oleamidopropyl betaine; oleamidopropyl hydroxysultaine; oleyl betaine; olivamide DEA; olivamidopropyl betaine; oliveamide MEA; palmamide DEA; palmamide MEA; palmamide MIPA; palmamidopropyl betaine; palmitamide DEA; palmitamide MEA; palmitamidopropyl betaine; palm kernel alcohol; palm kernelamide DEA; palm kernelamide MEA; palm kernelamide MIPA; palm kernelamidopropyl betaine; peanutamide MEA; peanutamide MIPA; pectin; PEG-800; PEG-crosspolymer; PEG-150/decyl alcohol/SMDI copolymer; PEG-175 diisostearate; PEG-190 distearate; PEG-15 glyceryl tristearate; PEG-140 glyceryl tristearate; PEG-240/HDI copolymer bis-decyltetradeceth-20 ether; PEG-100/IPDI copolymer; PEG-180/laureth-50/™MG copolymer; PEG-10/lauryl dimethicone crosspolymer; PEG-15/lauryl dimethicone crosspolymer; PEG-2M; PEG-5M; PEG-7M; PEG-9M; PEG-14M; PEG-20M; PEG-23M; PEG-25M; PEG-45M; PEG-65M; PEG-90M; PEG-115M; PEG-160M; PEG-180M; PEG-120 methyl glucose trioleate; PEG-180/octoxynol-40/™MG copolymer; PEG-150 pentaerythrityl tetrastearate; PEG-4 rapeseedamide; PEG-150/stearyl alcohol/SMDI copolymer; *phaseolus angularis* seed powder; *polianthes tuberosa* extract; polyacrylate-3; polyacrylic acid; polycyclopentadiene; polyether-1; polyethylene/isopropyl maleate/MA copolyol; polyglyceryl-3 disiloxane dimethicone; polyglyceryl-3 polydimethylsiloxyethyl dimethicone; polymethacrylic acid; polyquaternium-52; polyvinyl alcohol; potassium alginate; potassium aluminum polyacrylate; potassium carbomer; potassium carrageenan; potassium chloride; potassium palmate; potassium polyacrylate; potassium sulfate; potato starch modified; PPG-2 cocamide; PPG-1 hydroxyethyl caprylamide; PPG-2 hydroxyethyl cocamide; PPG-2 hydroxyethyl coco/isostearamide; PPG-3 hydroxyethyl soyamide; PPG-14 laureth-60 hexyl dicarbamate; PPG-14 laureth-60 isophoryl dicarbamate; PPG-14 palmeth-60 hexyl dicarbamate; propylene glycol alginate; PVP/decene copolymer; PVP montmorillonite; *pyrus cydonia* seed; *pyrus malus* (apple) fiber; rhizobian gum; ricebranamide DEA; ricinoleamide DEA; ricinoleamide MEA; ricinoleamide MIPA; ricinoleamidopropyl betaine; ricinoleic acid/adipic acid/AEEA copolymer; *rosa multiflora* flower wax; sclerotium gum; sesamide DEA; sesamidopropyl betaine; sodium acrylate/acryloyldimethyl taurate copolymer; sodium acrylates/acrolein copolymer; sodium acrylates/acrylonitrogens copolymer; sodium acrylates copolymer; sodium acrylates crosspolymer; sodium acrylate/sodium acrylamidomethylpropane sulfonate copolymer; sodium acrylates/vinyl isodecanoate crosspolymer; sodium acrylate/vinyl alcohol copolymer; sodium carbomer; sodium carboxymethyl chitin; sodium carboxymethyl dextran; sodium carboxymethyl beta-glucan; sodium carboxymethyl starch; sodium carrageenan; sodium cellulose sulfate; sodium chloride; sodium cyclodextrin sulfate; sodium hydroxypropyl starch phosphate; sodium isooctylene/MA copolymer; sodium magnesium fluorosilicate; sodium oleate; sodium palmitate; sodium palm kernelate; sodium polyacrylate; sodium polyacrylate starch; sodium polyacryloyldimethyl taurate; sodium polygamma-glutamate; sodium polymethacrylate; sodium polystyrene sulfonate; sodium silicoaluminate; sodium starch octenylsuccinate; sodium stearate; sodium stearoxy PG-hydroxyethylcellulose sulfonate; sodium styrene/acrylates copolymer; sodium sulfate; sodium tallowate; sodium tauride acrylates/acrylic acid/acrylonitrogens copolymer; sodium tocopheryl phosphate; *solanum tuberosum* (potato) starch; soyamide DEA; soyamidopropyl betaine; starch/acrylates/acrylamide copolymer; starch hydroxypropyltrimonium chloride; stearamide AMP; stearamide DEA; stearamide DEA-distearate; stearamide DIBA-stearate; stearamide MEA; stearamide MEA-stearate; stearamide MIPA; stearamidopropyl betaine; steareth-60 cetyl ether; steareth-100/PEG-136/HDI copolymer; stearyl alcohol; stearyl betaine; sterculia urens gum; synthetic fluorphlogopite; tallamide DEA; tallow alcohol; tallowamide DEA; tallowamide MEA; tallowamidopropyl betaine; tallowamidopropyl hydroxysultaine; tallowamine oxide; tallow betaine; tallow dihydroxyethyl betaine; *tamarindus indica* seed gum; tapioca starch; TEA-alginate; TEA-carbomer; TEA-hydrochloride; trideceth-2 carboxamide MEA; tridecyl alcohol; triethylene glycol dibenzoate; trimethyl pentanol hydroxyethyl ether; *triticum vulgare* (wheat) germ powder; *triticum vulgare* (wheat) kernel flour; *triticum vulgare* (wheat) starch; tromethamine acrylates/acrylonitrogens copolymer; tromethamine magnesium aluminum silicate; undecyl alcohol; undecylenamide DEA; undecylenamide MEA; undecylenamidopropyl betaine; welan gum; wheat germamide DEA; wheat germamidopropyl betaine; xanthan gum; yeast beta-glucan; yeast polysaccharides; *zea mays* (corn) starch; and blends thereof.

Also suitable as thickeners and/or viscosifiers are the following commercial products:

(1) Aqualon™ carboxymethylcellulose, Benecel™ methylcellulose and hydroxypropyl methylcellulose, Blanose™ sodium carboxymethylcellulose, Klucel™ hydroxypropylcellulose, Natrosol™ hydroxyethylcellulose, Natrosol™ Plus and PolySurf™ cetyl modified hydroxyethylcellulose, N-Hance™ cationic guar, N-Hance™ HP Series hydroxypropyl guar, N-Hance™ SP-100 conditioning polymer, and Supercol™ guar gum from Ashland Inc.

(2) Carbopol® Polymers, Fixate™ PLUS Polymer, Glucamate™ Thickeners, Amidex™ Surfactants, Chembetaine™ Surfactants, Chemoxide™ Surfactants, Chemonic™ Surfactants, Chemccinate™ Surfactants, Amidex™ BC-24 Surfactant, Chemoryl™ LB-30 Surfactant, Novethix™ L-10 Polymer, Ceralan™ Lanolin Product, Pemulen™ TR-1 Polymeric Emulsifier, Pemulen™ TR-2 Polymeric Emulsifier, Hydramol™ PGPD Ester, Schercodine™ M Amido-Amine, Schercodine™ P Amido-Amine, Schercomid™ Diethanolamides from The Lubrizol Corporation.

(3) Salcare® and Luvigel® from BASF Corporation.

(4) Aculyn™ 22, Aculyn™ 28, Aculyn™ 33, Aculyn™ 38, and Aculyn™ 44 from The Dow Chemical Company.

(5) Ammonyx® C and Stepan-Mild® GCC from Stepan Company.

(6) Stabileze®, Rapithix® A-60, Rapithix® A-100, Ultrathix® P-100, Lubrajel® and FlexiThix from International Specialty Products (Wayne, N.J.).

Also suitable as a thickener/rheology modifier are lightly- to moderately-crosslinked polyvinylpyrrolidones. Disclosures of these polymers are provided in the following publications, each of which is hereby incorporated in its entirety by reference: U.S. Pat. Nos. 5,073,614; 5,312,619; 5,139,770; 5,716,634; 5,470,884; 5,759,524; 5,997,887; 6,024,942; as well as international application PCT/US10/26973, PCT/US10/26976, PCT/US10/26940, PCT/US11/32993, and PCT/US11/34515.

Personal care compositions may comprise natural extracts and/or natural products. Extensive details on natural products that can be used in personal care compositions is provided in book chapter "Chemistry of Cosmetics, Comprehensive Natural Products II" in Chemistry and Biology; volume 3, 2010.

Oral Care Composition Ingredients

Oral care compositions may optionally contain one or more additional ingredients. Non-limiting examples of suitable ingredients include: carriers, dentifrices, cleaning agents, breath freshening actives, pain relievers, anesthetics, anti-inflammatory agents, antimicrobial agents, antibacterial agents, anti-calculus agents, anti-plaque agents, gums, thickeners, gelling agents, surfactants, flavors, warming or tingling agents, tooth bleaching agents, whiteners, stain removers, stain preventers, abrasives, adhesives, colors, emollients, emulsifiers, preservatives, solvents, binders, stimulants, depressants, diet aids, smoking cessation aides, vitamins, minerals, throat-soothing agents, spices, herbs, herbal extracts, alkaloids (such as caffeine and nicotine), and humectants.

The choice of a carrier to be used is basically determined by the way the composition is to be introduced into the oral cavity. Carrier materials for toothpaste, tooth gel or the like include abrasive materials, sudsing agents, binders, humectants, flavoring and sweetening agents, as disclosed in e.g., U.S. Pat. No. 3,988,433. Carrier materials for biphasic dentifrice formulations are disclosed in U.S. Pat. Nos. 5,213,790; 5,145,666; 5,281,410; 4,849,213; and 4,528,180. Mouthwash, rinse or mouth spray carrier materials typically include water, flavoring and sweetening agents, etc., as disclosed in, e.g., U.S. Pat. No. 3,988,433. Lozenge carrier materials typically include a candy base; chewing gum carrier materials include a gum base, flavoring and sweetening agents, as in, e.g., U.S. Pat. No. 4,083,955. Sachet carrier materials typically include a sachet bag, flavoring and sweetening agents. For sub-gingival gels used for delivery of actives into the periodontal pockets or around the periodontal pockets, a "sub-gingival gel carrier" is chosen as disclosed in, e.g., U.S. Pat. Nos. 5,198,220 and 5,242,910. The selection of a carrier will depend on secondary considerations like taste, cost, and shelf stability, and other factors.

Oral care compositions may comprise one or more dental abrasives. Dental abrasives useful in the compositions include many different materials. The material selected must be one which is compatible within the composition of interest and does not excessively abrade dentin.

Non-limiting examples of suitable abrasives include: silicas including gels and precipitates, insoluble sodium polymetaphosphate, hydrated alumina, calcium carbonate, dicalcium orthophosphate dihydrate, calcium pyrophosphate, tricalcium phosphate, calcium polymetaphosphate, resinous abrasive materials such as particulate condensation products of urea and formaldehyde, and blends thereof.

Another class of abrasives is the particulate thermosetting polymerized resins as described in U.S. Pat. No. 3,070,510, the contents of which are hereby incorporated by reference.

Non-limiting examples of suitable resins include: melamines, phenolics, ureas, melamine-ureas, melamine-formaldehydes, urea-formaldehyde, melamine-urea-formaldehydes, cross-linked epoxides, cross-linked polyesters, and blends thereof.

Silica dental abrasives of various types may be employed because of their unique benefits of exceptional dental cleaning and polishing performance without unduly abrading tooth enamel or dentine. The silica abrasive polishing materials herein, as well as other abrasives, generally have an average particle size ranging from about 0.1 to about 30 microns, and particularly from about 5 to about 15 microns. The abrasive can be precipitated silica or silica gels such as the silica xerogels described in U.S. Pat. No. 3,538,230 and U.S. Pat. No. 3,862,307.

Non-limiting examples of suitable silica abrasives include: silica xerogels marketed under the trade name "Syloid" by the W.R. Grace & Company, Davison Chemical Division and precipitated silica materials such as those marketed by the J.M. Huber Corporation under the trade name, Zeodent®, particularly the silicas carrying the designation Zeodent® 119, Zeodent® 118, Zeodent® 109 and Zeodent® 129. The types of silica dental abrasives useful in the toothpastes of the invention are described in more detail in U.S. Pat. Nos. 4,340,583; 5,603,920; 5,589,160; 5,658,553; 5,651,958; and 6,740,311. Each of these disclosures is hereby incorporated in its entirety by reference.

Mixtures of abrasives can be used such as mixtures of the various grades of Zeodent® silica abrasives listed above.

The total amount of abrasive(s) in the oral care compositions typically range from about 6% to about 70% by weight; toothpastes may contain from about 10% to about 50% of abrasives by weight of the composition. Dental solution, mouth spray, mouthwash and non-abrasive gel compositions typically contain little or no abrasives.

Oral care compositions may comprise polymeric mineral surface active agent(s) (PMSAs). PMSAs include any agent which will have a strong affinity for the tooth surface, deposit a polymer layer or coating on the tooth surface and produce the desired surface modification effects. The "mineral" descriptor is intended to convey that the surface activity or substantivity of the polymer is toward mineral surfaces such as calcium phosphate minerals or teeth.

Non-limiting examples of suitable PMSAs include: polyelectrolytes such as condensed phosphorylated polymers; polyphosphonates; copolymers of phosphate- or phosphonate-containing monomers or polymers with other monomers such as ethylenically unsaturated monomers and amino acids or with other polymers such as proteins, polypeptides, polysaccharides, poly(acrylate), poly(acrylamide), poly(methacrylate), poly(ethacrylate), poly(hydroxyalkylmethacrylate), poly(vinyl alcohol), poly(maleic anhydride), poly(maleate) poly(amide), poly(ethylene amine), poly(ethylene glycol), poly(propylene glycol), poly(vinyl acetate), poly(vinyl benzyl chloride), polycarboxylates, carboxy-substituted polymers, and blends thereof. Also suitable as polymeric mineral surface active agents are the carboxy-substituted alcohol polymers described in U.S. Pat. Nos. 5,292,501; 5,213,789, 5,093,170; 5,009,882; and 4,939,284; and the diphosphonate-derivatized polymers in U.S. Pat. No. 5,011,913; the synthetic anionic polymers including polyacrylates and copolymers of maleic anhydride or acid and methyl vinyl ether (e.g., Gantrez®), as described, for example, in U.S. Pat. No. 4,627,977. Another example of a polymeric mineral surface active agent is a diphosphonate modified polyacrylic acid.

Polymers with activity must have sufficient surface binding propensity to desorb pellicle proteins and remain affixed to enamel surfaces. For tooth surfaces, polymers with end or side chain phosphate or phosphonate functions may be used, although other polymers with mineral binding activity may prove effective depending upon adsorption affinity.

PMSAs are useful in the compositions because of their stain prevention benefit. It is believed the PMSAs provide a stain prevention benefit because of their reactivity or substantivity to mineral surfaces, resulting in desorption of portions of undesirable adsorbed pellicle proteins, in particular those associated with binding color bodies that stain teeth, calculus development and attraction of undesirable microbial species. The retention of these PMSAs on teeth can also prevent stains from accruing due to disruption of binding sites of color bodies on tooth surfaces.

The ability of PMSA to bind stain promoting ingredients of oral care products such as stannous ions and cationic antimicrobials is also believed to be helpful. The PMSA will also provide tooth surface conditioning effects which produce desirable effects on surface thermodynamic properties and surface film properties, which impart improved clean feel aesthetics both during and most importantly, following rinsing or brushing. Many of these polymeric agents are also known or expected to provide tartar control benefits when applied in oral compositions, hence providing improvement in both the appearance of teeth and their tactile impression to consumers. The desired surface effects may include: 1)

creating a hydrophilic tooth surface immediately after treatment; and 2) maintaining surface conditioning effects and control of pellicle film for extended periods following product use, including post brushing or rinsing and throughout more extended periods. The effect of creating an increased hydrophilic surface can be measured in terms of a relative decrease in water contact angles. The hydrophilic surface, importantly, is maintained on the tooth surface for an extended period after using the product.

Oral care compositions may comprise additional anticalculus agent(s), such as a pyrophosphate salt as a source of pyrophosphate ion.

Non-limiting examples of suitable pyrophosphate salts include: dialkali metal pyrophosphate salts, tetraalkali metal pyrophosphate salts, and mixtures thereof. Particularly, disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms may find utility.

In compositions of the invention, the pyrophosphate salt may be present in one of three ways: predominately dissolved, predominately undissolved, or a mixture of dissolved and undissolved pyrophosphate.

Compositions comprising predominately dissolved pyrophosphate refer to compositions where at least one pyrophosphate ion source is in an amount sufficient to provide at least about 1.0% free pyrophosphate ions. The amount of free pyrophosphate ions may be from about 1% to about 15%, particularly from about 1.5% to about 10%, and more particularly from about 2% to about 6%. Free pyrophosphate ions may be present in a variety of protonated states depending on the pH of the composition.

Compositions comprising predominately undissolved pyrophosphate refer to compositions containing no more than about 20% of the total pyrophosphate salt dissolved in the composition, particularly less than about 10% of the total pyrophosphate dissolved in the composition. Tetrasodium pyrophosphate salt may be one such pyrophosphate salt in these compositions. Tetrasodium pyrophosphate may be the anhydrous salt form or the decahydrate form, or any other species stable in solid form in the oral care compositions. The salt is in its solid particle form, which may be its crystalline and/or amorphous state, with the particle size of the salt being small enough to be aesthetically acceptable and readily soluble during use. The amount of pyrophosphate salt useful in making these compositions is any tartar control effective amount, generally from about 1.5% to about 15%, particularly from about 2% to about 10%, and more particularly from about 3% to about 8% by weight of the oral care composition.

The pyrophosphate salts are described in more detail in Kirk-Othmer Encyclopedia of Chemical Technology, third edition, volume 17, Wiley-Interscience Publishers (1982).

Oral care compositions may comprise peroxide compounds.

Non-limiting examples of suitable peroxide compounds include: hydrogen peroxide and organic peroxides including urea peroxide, carbamide peroxide, glyceryl peroxide, benzoyl peroxide, derivatives thereof, and blends thereof.

Typically, the peroxide compound can be employed in amounts so that at least about 1% by weight of the composition comprises peroxide. The peroxide compound may comprise from about 2% to about 30% by weight of the composition. More particularly, the peroxide comprises from about 3% to about 15% by weight of the composition. A typical peroxide concentration in the composition is generally from about 2% to about 7% by weight for home use products, and from about 15% to about 20% by weight for dental professional use.

Thickening or gelling agents used in dentifrice compositions may include nonionic polyoxyethylene polyoxypropylene block copolymers. Illustrative of polyoxyethylene polyoxypropylene block copolymers useful in the practice include block copolymers having the formula $HO(C_2H_4O)_b(C_3H_6O_6)_a(C_2H_4O)_bH$ wherein a is an integer such that the hydrophobic base represented by $(C_3H_6O_6)$ has a molecular weight of about 2,750 Da to 4000 Da, b is an integer such that the hydrophilic portion (moiety) represented by $(C_2H_4O)$ constitutes from about 70% to about 80% by weight of the copolymer. Block copolymers of this composition are available commercially under the trademark Pluronic® F type.

Pluronic® F127 has a molecular weight of 4,000 Da and contains 70% of the hydrophilic polyoxyethylene moiety.

Also suitable as a thickening agent is lightly- to moderately-crosslinked PVP, described in international application PCT/US11/30642, the contents of which are hereby incorporated by reference.

The thickening agents may be present in an amount from about 15% to about 50% by weight, particularly from about 25% to about 45% by weight of the composition.

Surfactants may also be included in the oral care compositions of the invention, where they may serve in solubilizing, dispersing, emulsifying and/or reducing the surface tension of the teeth in order to increase the contact between the tooth and the peroxide. The compositions may also comprise surfactants, also commonly referred to as sudsing agents. Suitable surfactants are those which are reasonably stable and foam throughout a wide pH range. Surfactants may be chosen from anionic, nonionic, amphoteric, zwitterionic, or cationic surfactants, or blends thereof.

Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate (SLS) and sodium coconut monoglyceride sulfonates are non-limiting examples of anionic surfactants of this type. Many suitable anionic surfactants are disclosed in U.S. Pat. No. 3,959,458. The compositions may comprise an anionic surfactant in an amount from about 0.025% to about 9% by weight, particularly from about 0.05% to about 5% by weight, and more particularly from about 0.1% to about 1% by weight of the composition.

Non-limiting examples of suitable anionic surfactants include: sarcosinates, taurates, isethionates, sodium lauryl sulfoacetate, sodium laureth carboxylate, and sodium dodecyl benzenesulfonate. Also suitable are alkali metal or ammonium salts of surfactants such as the sodium and potassium salts of the following: lauroyl sarcosinate, myristoyl sarcosinate, palmitoyl sarcosinate, stearoyl sarcosinate, and oleoyl sarcosinate. The sarcosinate surfactant may be present in the compositions from about 0.1% to about 2.5%, particularly from about 0.5% to about 2.0% by weight of the total composition.

Non-limiting examples of suitable cationic surfactants include: derivatives of aliphatic quaternary ammonium compounds having at least one long alkyl chain containing from about 8 to about 18 carbon atoms such as lauryl trimethylammonium chloride, cetyl pyridinium chloride, cetyl trimethylammonium bromide, di-isobutylphenoxyethyl-dimethylbenzylammonium chloride, coconut alkyltrimethylammonium nitrite, cetyl pyridinium fluoride, and blends thereof. Also suitable are the quaternary ammonium fluorides described in U.S. Pat. No. 3,535,421, where the quaternary ammonium fluorides have detergent properties. Certain cationic surfactants can also act as germicides in the compositions disclosed herein.

Nonionic surfactants that may be used in the compositions of the invention include compounds produced by the condensation of alkylene oxide groups (hydrophilic in nature) with an organic hydrophobic compound which may be aliphatic or alkylaromatic in nature.

Non-limiting examples of suitable nonionic surfactants include: poloxamers (sold under the trade name Pluronic® by BASF Corporation), polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and blends thereof.

Non-limiting examples of suitable zwitterionic surfactants include betaines and derivatives of aliphatic quaternary ammonium compounds in which the aliphatic radicals can be straight chain or branched, and which contain an anionic water-solubilizing group, e.g., carboxy, sulfonate, sulfate, phosphate, or phosphonate.

Non-limiting examples of suitable betaines include: decyl betaine or 2-(N-decyl-N,N-dimethylammonio)acetate, coco betaine or 2-(N-coc-N,N-dimethyl ammonio)acetate, myristyl betaine, palmityl betaine, lauryl betaine, cetyl betaine, stearyl betaine, and blends thereof. The amidobetaines are exemplified by cocoamidoethyl betaine, cocoamidopropyl betaine, lauramidopropyl betaine, and the like. The betaines of choice include cocoamidopropyl betaines such as lauramidopropyl betaine. Suitable betaine surfactants are disclosed in U.S. Pat. No. 5,180,577.

Other surfactants such as fluorinated surfactants may also be incorporated within the compositions of the invention.

Oral care compositions may comprise flavor(s). Non-limiting examples of suitable flavors include: methyl salicylate, ethyl salicylate, methyl cinnamate, ethyl cinnamate, butyl cinnamate, ethyl butyrate, ethyl acetate, methyl anthranilate, iso-amyl acetate, iso-armyl butyrate, allyl caproate, eugenol, eucalyptol, thymol, cinnamic alcohol, cinnamic aldehyde, octanol, octanal, decanol, decanal, phenylethyl alcohol, benzyl alcohol, benzaldehyde, α-terpineol, linalool, limonene, citral, vanillin, ethyl vanillin, propenyl guaethol, maltol, ethyl maltol, heliotropin, anethole, dihydroanethole, carvone, oxanone, menthone, β-damascenone, ionone, gamma decalactone, gamma nonalactone, gamma undecalactone, 4-hydroxy-2,5-dimethyl-3(2H)-furanone, and blends thereof.

Generally suitable flavoring agents are those containing structural features and functional groups that are less prone to oxidation by peroxide. These include derivatives of flavor chemicals that are saturated or contain stable aromatic rings or ester groups.

Also suitable are flavor chemicals that may undergo some oxidation or degradation without resulting in a significant change in the flavor character or profile. The flavor chemicals, including menthol, may be provided as single or purified chemicals rather than supplied in the composition by addition of natural oils or extracts such as peppermint, spearmint, or wintergreen oils as these sources may contain other components that are relatively unstable and may degrade in the presence of peroxide. Flavoring agents are generally used in the compositions at levels of from about 0.001% to about 5% by weight of the composition.

The flavor system may typically include sweetening agent(s). Sweeteners include compounds of natural and artificial origin.

Non-limiting examples of suitable water-soluble natural sweeteners include: monosaccharides, disaccharides and polysaccharides, such as xylose, ribose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochalcones, monellin, steviosides, glycyrrhizin, and blends thereof.

Non-limiting examples of suitable water-soluble artificial sweeteners include: soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (acesulfame-K), the free acid form of saccharin, and the like. Other suitable sweeteners include dipeptide based sweeteners, such as L-aspartic acid derived sweeteners, such as L-aspartyl-L-phenylalanine methyl ester (aspartame) and materials described in U.S. Pat. No. 3,492,131, L-α-aspartyl-N-(2,2,4,4-tetramethyl-3-thietanyl)-D-alaninamide hydrate, methyl esters of L-aspartyl-L-phenylglycerin and L-aspartyl-L-2,5,dihydrophenyl-glycine, L-aspartyl-2,5-dihydro-L-phenylalanine, L-aspartyl-L-(1-cyclohexyen)-alanine, derivatives thereof, and blends thereof. Water-soluble sweeteners derived from naturally occurring water-soluble sweeteners, such as a chlorinated derivative of ordinary sugar (sucrose), known, for example, under the product description of sucralose as well as protein based sweeteners such as thaumatoccous danielli (Thaumatin I and II) may be used. The compositions may contain sweetener(s) in an amount from about 0.1% to about 10% by weight, in particular from about 0.1% to about 1% by weight of the composition.

In addition, the flavor system may include salivating agents, warming agents, and numbing agents. These agents are present in the compositions in an amount from about 0.001% to about 10% by weight, particularly from about 0.1% to about 1% by weight of the composition.

A non-limiting example of suitable salivating agent includes Jambus® manufactured by Takasago. Non-limiting examples of suitable warming agents include *capsicum* and nicotinate esters such as benzyl nicotinate. Non-limiting examples of suitable numbing agents include benzocaine, lidocaine, clove bud oil, ethanol, and blends thereof.

Oral care compositions may comprise chelating agent(s).

The chelating agents may include metal solubilizing agents and metal precipitating agents. The metal solubilizing agents include a condensed pyrophosphate compound. For purposes of this invention "condensed phosphate" relates to an inorganic phosphate composition containing two or more phosphate species in a linear or cyclic pyrophosphate form. The condensed phosphate may be sodium pyrophosphate, but may also include tripolyphosphate, hexametaphosphate, cyclic condensed phosphate or other similar phosphates well known in the field. The blend may also include an organic chelating agent. The term "organic phosphate" includes phosphonic acid, di and tri phosphonoc acid compound or its salts. An example of phosphonic acid is 1-hydroxyethylidene-1,1-diphosphonic acid that is sold under the trade name of Dequest®. The blend may also include a metal precipitating chelating agent. The term "metal precipitating chelating agent" is an agent that binds to metals and causes the metal to precipitate and includes halogens such as fluoride. The chelating agents are incorporated in the oral care compositions of the invention in an amount from about 0.1% to about 8.0% by weight, and particularly from about 0.5% to about 3.0% by weight of the composition, in a ratio of about 3:1:1 w/w organic chelating agent: condensed phosphate chelating agent: metal precipitating agent.

Another optional ingredient that may be used in oral care compositions is a humectant. For example, a humectant may be added to keep toothpaste compositions from hardening upon exposure to air, to give compositions a moist feel to the mouth, and, for particular humectants, to impart desirable sweetness of flavor to toothpaste compositions. The humectant, on a pure humectant basis, is generally present from about 0% to about 70%, particularly from about 5% to about 25% by weight of the composition.

Non-limiting examples of suitable humectants include: edible polyhydric alcohols such as glycerin, sorbitol, xylitol, butylene glycol, polyethylene glycol, propylene glycol, trimethyl glycine, and blends thereof.

The invention also contemplates oral care compositions comprising polymer(s) described herein complexed with hydrogen peroxide. A description of such complexes is present in international application WO 91/07184, the contents of which are hereby incorporated in their entirety by reference.

Also contemplated are oral care compositions such as those described in the following patents and patent applications, the contents of each are hereby incorporated in their entirety by reference: WO 2011/068514, WO 2011/053877, US 2010/0275394, US 2011/0076090, US 2008/091935, US 2008/0181716, US 2008/0014224, WO 2007/066837, US 2008/0292669, US 2007/0071696, US 2007/0154863, US 2008/0317797, US 2005/0249678, US 2007/0178055, US 2007/0189983, WO 2005/041910, U.S. Pat. No. 7,785,572, WO 1998/005749, WO 1997/022651, and U.S. Pat. No. 5,310,563.

Oral care compositions may comprise one or more denture adhesives.

Synthetic materials presently dominate the denture adhesive market. Such materials may consist of mixtures of the salts of short-acting polymers (e.g., carboxymethylcellulose or "CMC") and long-acting polymers (e.g., poly(vinyl methyl ether maleate), or "Gantrez" and its salts). Polyvinylpyrrolidone (povidone) may also be used.

Other components of denture adhesive products impart particular physical attributes to the formulations. Petrolatum, mineral oil, and polyethylene oxide may be included in creams to bind the materials and to make their placement easier. Silicon dioxide and calcium stearate may be used in powders to minimize clumping. Menthol and peppermint oils may be used for flavoring, red dye for color, and sodium borate and methyl- or poly-paraben as preservatives.

The synthesis of the degradable compounds, which may be coupled with a wide variety of monomers to form functionalized polymers, can be prepared according to the examples set out below. The examples are presented for purposes of demonstrating, but not limiting, the preparation of the compounds and compositions of this invention.

EXAMPLES

In accordance with the invention, the following examples are provided to illustrate methods for preparing the degradable compounds, monomers, and polymers.

Instrumentation $^1H/^{13}C$ NMR was recorded using a Bruker Avance-400, Varian iNova-500 or Varian VNMRS 700 operating at 400, 500, and 700 MHz, respectively, J values are given in Hz. Low-resolution mass spectroscopy (MS) was recorded using a Micromass LCT ToF, all recorded as ES$^+$ CHN analysis was carried out on an Exeter Analytical Inc. C6-440 Elemental Analyzer. GPC data was obtained using a Viscotek TDA 302 using 2×300 mL PLgel 5 μm mixed C columns and DMF (containing 0.1% w/v LiBr) as the eluent (flow rate of 1 mL/min) Refractive index (RI), viscosity and light scattering detectors were used to determine molecular weights. These detectors were calibrated using narrow molecular weight distribution polystyrene as a standard with a dn/dc (differential index of refraction) of 0.165 mL/g. The differential index of refraction of a material is a measure of how the RI changes with concentration. Polystyrene was used as a suitable estimation to gain information on the molecular weight distribution of the polymers. Further for the co-polymers synthesized, the dn/dc values would change as the composition of the co-polymer altered. Using a polystyrene standard is therefore the best way to obtain results for these compounds.

Comparative Example 1

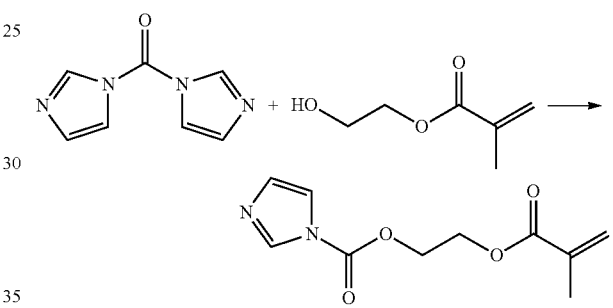

1,1'-Carbonyldiimidazole (CDI) (10 g, 61.6 mmol, 2 eq) was added to a 250 mL, 3 necked round bottom flask fitted with a reflux condenser, dry nitrogen inlet and magnetic stirrer bar. The system was purged with nitrogen for 30 min. Dry toluene (20 mL) was added. Hydroxyethyl methacrylate (HEMA) (4 g, 30.8 mmol, 1 eq) was added dropwise and the mixture stirred for 60 min. The solution was washed with several portions of water until the washings were neutral. The organic phase was collected and dried over MgSO$_4$. The solvent was removed at reduced pressure to give the product; Yield 49.7% (3.316 g, 14.8 mmol). The structure of the compound was confirmed by elemental analysis, mass spectroscopy (MS), $^1$H NMR, and $^{13}$C NMR.

Example 1

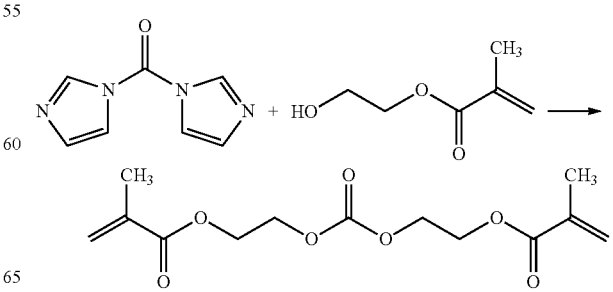

CDI (5 g, 30.8 mmol, 1 eq) was added to a 250 mL, 3-necked round-bottomed flask fitted with a condenser and dry nitrogen inlet and magnetic stirrer bar. The system was purged with nitrogen for 30 min. Dry toluene (20 mL) was added. HEMA (8.3 g, 63.5 mmol, 2 eq) was added dropwise and the mixture was stirred for 60 minutes. The solution was washed with several portions of water until the washings were neutral. The organic layer was collected and dried over MgSO₄. The solvent was removed at reduced pressure to give the product; Yield 57.4% (5.024 g, 17.5 mmol). The structure of the compound was confirmed by elemental analysis, mass spectroscopy (MS), $^1$H NMR, and $^{13}$C NMR.

Comparative Example 2

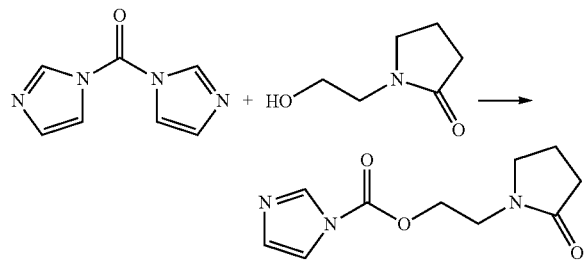

Dry toluene (30 mL) was added to a 250 mL, 3-necked round-bottomed flask fitted with a condenser, dry nitrogen inlet and magnetic stirrer bar. The system was purged with nitrogen for 30 min. CDI (5 g, 30.8 mmol, 2 eq), KOH (0.017 g) and HEP (1.989 g, 15.4 mmol, 1 eq) were added. The mixture was stirred for 18 hr. The flask was placed in ice and imidazole solid removed via filtration. Any residual imidazole was removed using a basic alumina pipette column. The organic phase was collected and the solvent removed under reduced pressure to give the product; Yield 50.4% (1.731 g, 7.8 mmol). The structure of the compound was confirmed by mass spectroscopy (MS), $^1$H NMR, and $^{13}$C NMR.

Example 2

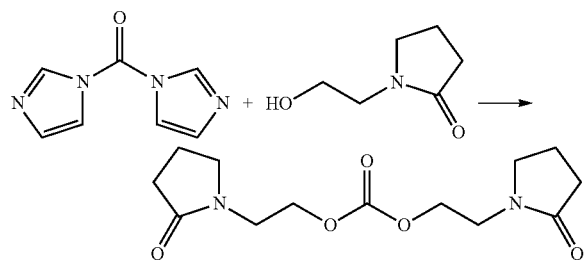

Dry toluene (20 mL) was added to a 100 mL 3-necked multi-necked round-bottomed flask fitted with a condenser, dry nitrogen inlet and magnetic stirrer bar. The system was purged with nitrogen for 30 min. CDI (5 g, 30.8 mmol, 1 eq) and HEP (8.2 g 63.5 mmol) were added and the mixture was heated in an oil bath with stirring at 60° C. for 4½ hours. Amberlyst 15 (~3 g) was added and the mixture was stirred for ~1 hour. The solid was removed by filtration and the solvent was removed under reduced pressure to give the product; Yield 68.8% (6.023 g, 21.18 mmol). The structure of the compound was confirmed by elemental analysis, mass spectroscopy (MS), $^1$H NMR, and $^{13}$C NMR.

Comparative Example 3

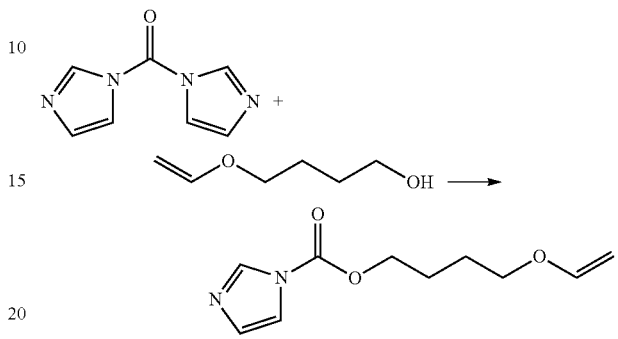

Dry toluene (40 mL) was added to a 250 mL, 3-necked round-bottomed flask fitted with a condenser, dry nitrogen inlet and magnetic stirrer bar. The system was purged with nitrogen for 30 min. CDI (5 g, 30.8 mmol, 2 eq), KOH (0.020 g) and 1,4-butanediol vinyl ether (1.70 g, 14.6 mmol, 1 eq) were added to the flask. The mixture was stirred for 15 hours. The flask was placed in ice and the solid removed by filtration. The solution was washed with a small amount of water. The organic phase was collected and dried over MgSO₄. The solvent was removed under reduced pressure to give the product; Yield 46.9% (1.506 g, 7.16 mmol). The structure of the compound was confirmed by $^1$H NMR, and $^{13}$C NMR.

Example 3

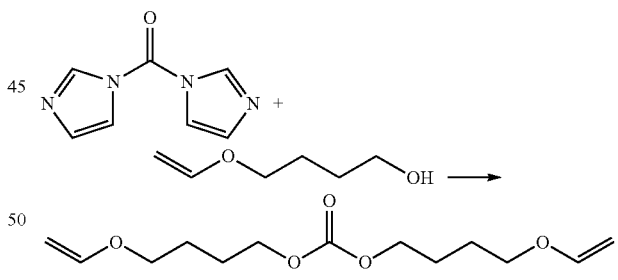

Dry toluene (20 mL) was added to a 250 mL, 3-necked round-bottomed flask fitted with a condenser, dry nitrogen inlet and magnetic stirrer bar. The system was flushed with nitrogen for 30 min. CDI (5 g, 30.8 mmol, 1 eq), KOH (0.015 g) and 1,4-butanediol vinyl ether (7.79 g, 67 mmol, 2 eq) were added to the flask and the mixture was stirred 15 hours. The flask was cooled in ice and the resulting solid removed by filtration. Residual imidazole and 1,4-butanediol vinyl ether removed using a basic alumina pipette column. The solvent was removed under reduced pressure to give the product; Yield 31.3% (2.488 g, 9.63 mmol). The structure of the compound was confirmed by $^1$H NMR, and $^{13}$C NMR.

Example 4

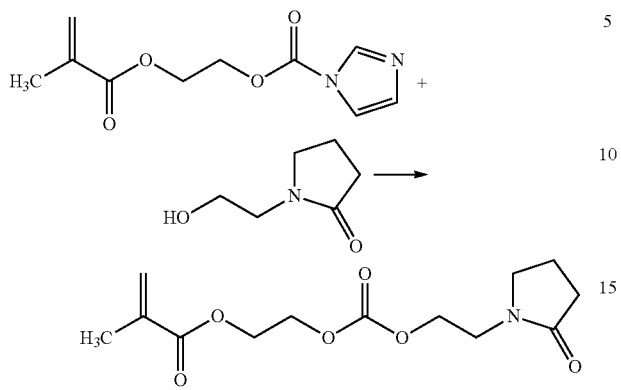

2-[(1-Imidazolyl)formyloxy]ethyl methacrylate (9.42 g, 42 mmol, 1 eq), dry toluene (5 mL), KOH (0.010 g) and HEP (5.696 g, 49.1 mmol, 1 eq) were added to a 50 mL, 2-necked round bottomed flask fitted with a condenser and magnetic stirrer bar. The mixture was stirred at RT for 18 hours and filtered to remove any solids. The product was further purified using a basic alumina column. Solvent was removed under reduced pressure to give the product; Yield 30.0% (3.592 g, 12.59 mmol). The structure of the compound was confirmed by elemental analysis, mass spectroscopy (MS), $^1$H NMR, and $^{13}$C NMR.

Example 5

Free Radical Homopolymerization of the HEMA-HEP Carbonate Monomer

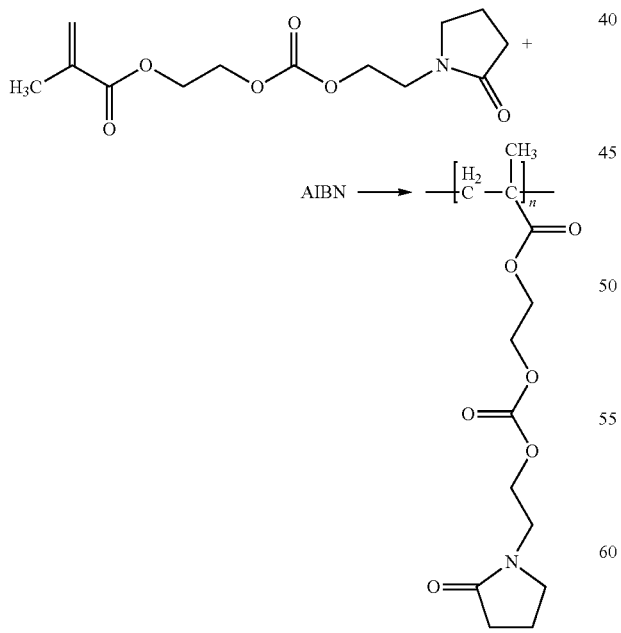

The HEMA-HEP carbonate monomer of Example 5 (0.9 g, 3.15 mmol), azobis(isobutyronitrile) (AIBN) (0.0072 g) and dry DMF (1.5 mL) were placed in an ampoule containing a magnetic stirrer bar. The mixture was degassed by 4 cycles of freeze-pump-thaw and the tube was sealed under vacuum. The solution was heated with stirring at 70° C. for 4 hours. The solvent was removed under reduced pressure. Chloroform (~100 mL) was added and the mixture was added dropwise to diethyl ether to precipitate the polymer. The polymer was isolated by vacuum filtration and dried in a vacuum oven to give the product; Conversion 83% (0.75 g). The structure of the compound was confirmed by $^1$H NMR. The structural subscript n is an integer equal to or greater than 1 such that the number of monomer units yields a polymer having a molecular weight ranging from 500 Da to about 5,000,000 Da.

Example 6

Controlled Radical Homopolymerization of the HEMA-HEP Carbonate Monomer Using Reversible Addition-Fragmentation Chain Transfer Polymerization (RAFT)

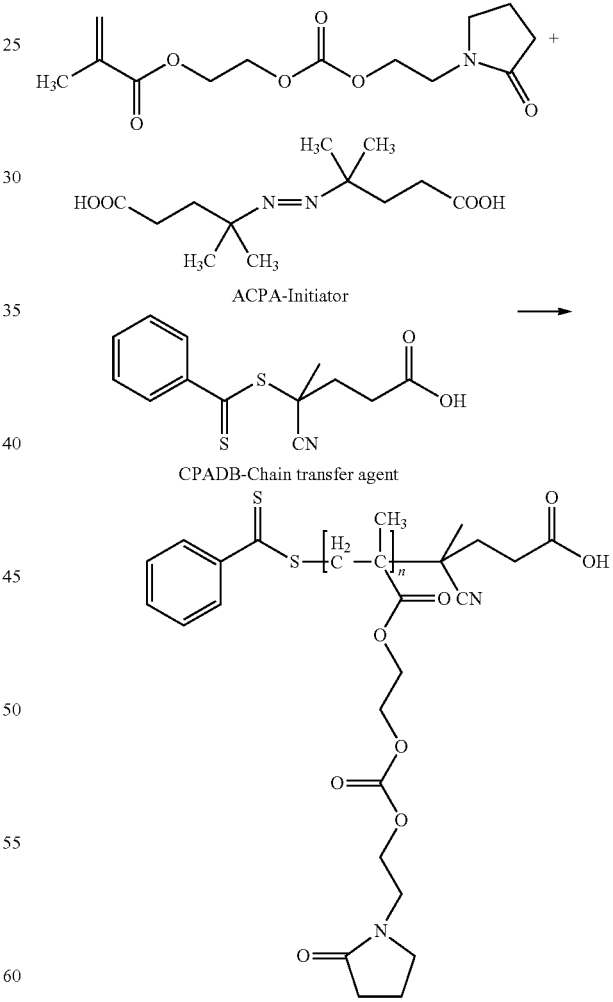

The HEMA-HEP carbonate monomer of Example 5 (0.9 g, 3.15 mmol), 4,4'-azobis(4-cyanopentanoic acid) (ACPA) (0.0176 g, 0.0063 mmol), 4-cyanopentanoic acid dithiobenzoate (CPADB) (0.0042 g 0.0016 mmol), and dry DMF (1.5 mL) were placed in an ampoule containing a magnetic stirrer bar. The mixture was degassed by 4 cycles of freeze-pump-thaw and placed under a flow of nitrogen. The solution was heated at 70° C. for 4 hours. The resulting polymer was recovered by precipitation in diethyl ether followed by vacuum filtration. The solid was dried in a vacuum oven to give the product; Conversion 4.2% (0.038 g). The structure of the compound was confirmed by $^1$H NMR. The structural subscript n is an integer equal to or greater than 1 such that the number of monomer units yields a polymer having a molecular weight ranging from 500 Da to about 5,000,000 Da.

Example 7

Random Co-Polymerization of the HEMA-HEP Carbonate Monomer with Vinyl Acetate

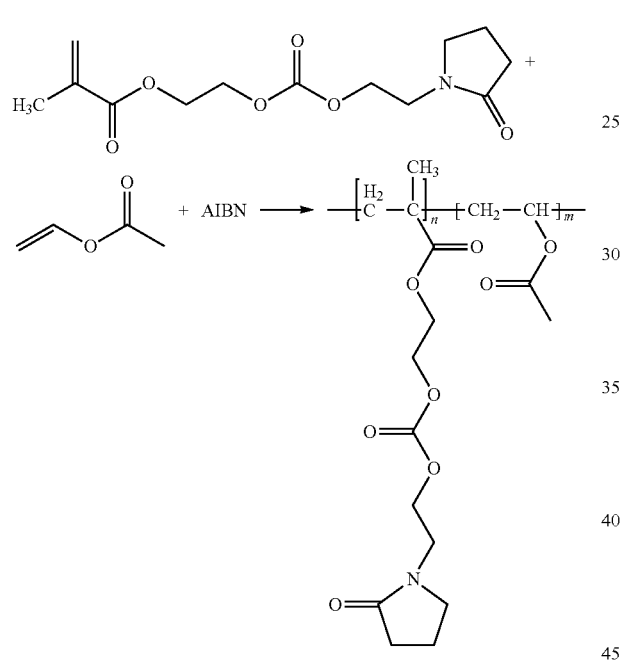

The HEMA-HEP carbonate monomer of Example 5 (0.3 g, 1.05 mmol), vinyl acetate (0.2713 g, 3.15 mmol), AIBN (0.00345 g, 21×10$^{-3}$ mmol) and ethanol (1.5 mL) were placed in a Schlenk tube with a magnetic stirrer bar. The mixture was degassed with 4 cycles of freeze-pump-thaw and sealed under nitrogen. The flask was heated in an oil bath to 61° C. and stirred for 17 hours. The solution was cooled, ethanol (1.5 mL) was added and the mixture was reheated to 61° C., the solution was precipitated while warm, into diethyl ether. The mixture was filtered. The solid was dried in a vacuum oven to give the product; Conversion 27.3% (0.156 g). The structure of the compound was confirmed by $^1$H NMR. The structural subscripts m and n are integers equal to or greater than 1 such that the number of monomer units yields a polymer having a molecular weight ranging from 500 Da to about 5,000,000 Da.

The experiment was repeated using DMF (1.5 mL) as solvent. The product was precipitated in water to give the product; Conversion 38.5% (0.22 g). The structure of the compound was confirmed by $^1$H NMR.

Example 8

Co-Polymerization of the HEMA-HEP Carbonate Monomer with Vinyl Acetate

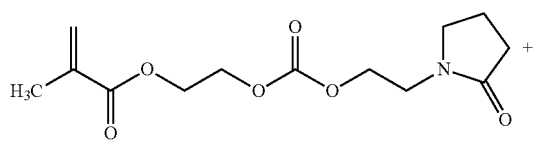

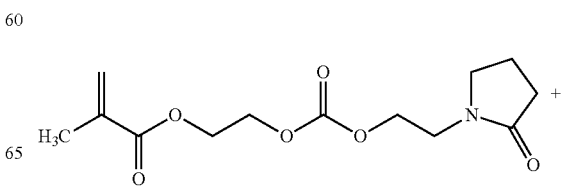

Co-polymerization reactions involving the HEMA-HEP carbonate monomer and vinyl acetate were run for ~16 hours. The feed ratio for the reactions involved a 50:150:1 ratio of HEMA-HEP:VAc:AIBN. The reaction was sealed under nitrogen and heated to ~61° C. (high enough to initiate the AIBN but not high enough to evaporate VAc). After isolation of the product, the $^1$H NMR confirmed the presence of PHEMA-HEP and PVAc. The structural subscripts m and n are integers equal to or greater than 1 such that the number of monomer units yields a polymer having a molecular weight ranging from 500 Da to about 5,000,000 Da.

Example 9

Random Co-Polymerization of the HEMA-HEP Carbonate Monomer and N-Vinyl-2-Pyrrolidone (NVP)

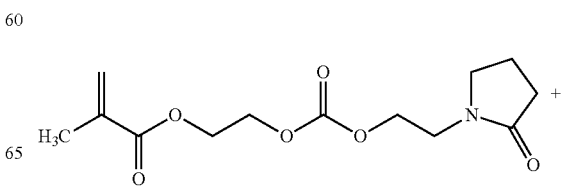

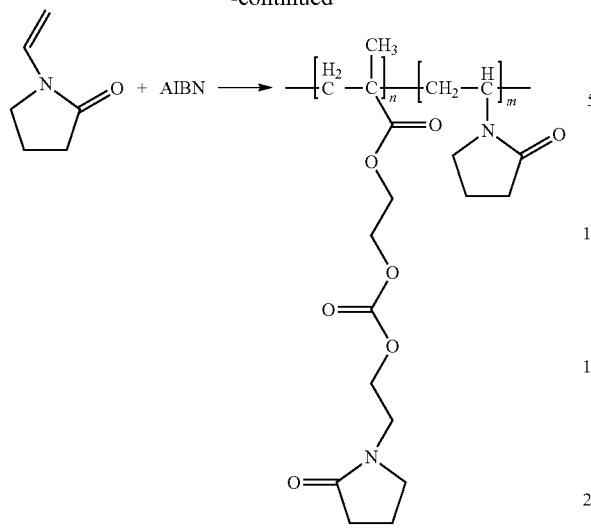
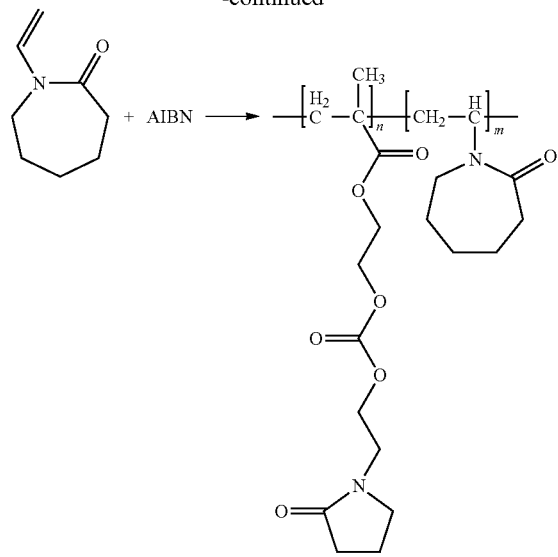

The HEMA-HEP carbonate monomer of Example 5 (0.3 g, 1.05 mmol), NVP (0.3501 g, 3.15 mmol), AIBN (0.00345 g, $21 \times 10^{-3}$ mmol) and ethanol (1.5 mL) were placed in a Schlenk tube containing a magnetic stirrer bar. The mixture was degassed using 4 cycles of freeze-pump-thaw and sealed under nitrogen. The flask was heated to 60° C. and the mixture stirred for 19 hours. The solution was cooled, ethanol (1.5 mL) was added and the solution re-heated. The product was isolated by precipitation into cool hexane. The hexane was decanted and the solid dried in a vacuum oven to give the product; Conversion 62.5% (0.406 g). The structure of the compound was confirmed by $^1$H NMR. The structural subscripts m and n are integers equal to or greater than 1 such that the number of monomer units yields a polymer having a molecular weight ranging from 500 Da to about 5,000,000 Da.

Example 10

Random Co-Polymerization of the HEMA-HEP Carbonate Monomer with N-Vinyl-2-Caprolactam (NVCL)

The HEMA-HEP carbonate monomer of Example 5 (0.3 g, 1.05 mmol), NVCL (0.4385 g, 3.15 mmol), AIBN (0.00345 g, $21 \times 10^{-3}$ mmol) and ethanol (1.5 mL) were added to a Schlenk tube containing a magnetic stirrer bar. The mixture was degassed using 4 cycles of freeze-pump-thaw and sealed under nitrogen. The flask was heated 60° C. and stirred for 19 hours. The solution was cooled; ethanol (1.5 mL) added and re-heated. The product was isolated by precipitation into cool hexane. The hexane was decanted and the solid dried in a vacuum oven to give the product; 57.1% (0.421 g). The structure of the compound was confirmed by $^1$H NMR. The structural subscripts m and n are integers equal to or greater than 1 such that the number of monomer units yields a polymer having a molecular weight ranging from 500 Da to about 5,000,000 Da.

Example 11

Block Co-Polymerization of the HEMA-HEP Carbonate Monomer with PVP Macro-Initiator

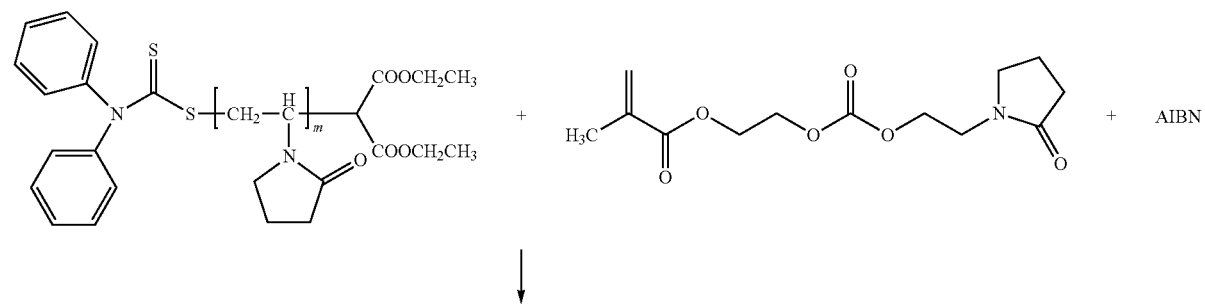

-continued

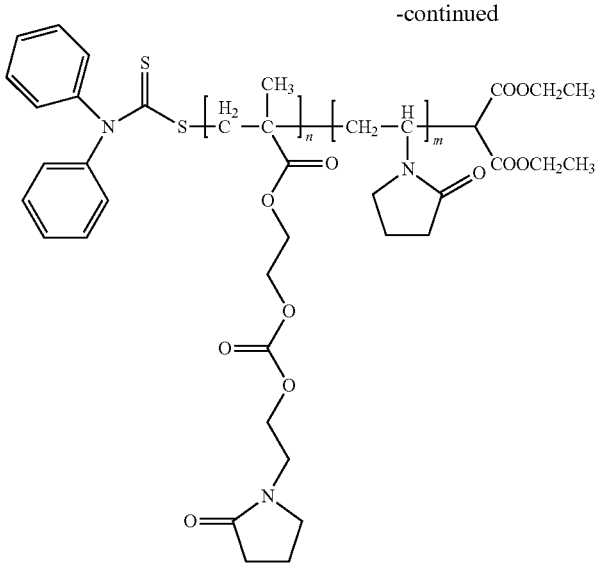

The HEMA-HEP carbonate monomer of Example 5 (0.51 g, 1.80 mmol), PVP (0.877 g, 7.19 mmol), AIBN (0.0242 g, 0.15 mmol) and dioxane (1.5 mL) were placed in a Schlenk tube containing a magnetic stirrer bar. The mixture was degassed using 3 cycles of freeze-pump-thaw and sealed under nitrogen. The flask was heated to 60° C. and the mixture was stirred for 16 hours. The solution was cooled. The product was precipitated into cool diethyl ether. The solid was isolated by filtration and dried in a vacuum oven to give the product; Conversion 61.1% (0.8471 g). The structure of the compound was confirmed by $^1$H NMR. The structural subscripts m and n are integers equal to or greater than 1 such that the number of monomer units yields a polymer having a molecular weight ranging from 500 Da to about 5,000,000 Da.

Comparative Example 4

Homopolymerization of HEMA

Hydroquinone inhibitor was removed from HEMA prior to use by a basic alumina column. The HEMA (0.70 g, 5.38 mmol), AIBN (0.0044 g, 0.027 mmol) and ethanol (1.5 mL) were placed in a Schlenk tube containing a magnetic stirrer bar. The mixture was degassed using 3 cycles of freeze-pump-thaw and sealed under nitrogen. The flask was heated to 60° C. and the mixture stirred for 17 hours. The solution was cooled. The product was dissolved in methanol and precipitated in to cool diethyl ether. The solid was isolated by filtration and dried in a vacuum oven to give the product. Because the product was insoluble in deuterated solvents, NMR analysis was not possible.

While a number of embodiments of this invention have been represented, it is apparent that the basic construction can be altered to provide other embodiments that utilize the invention without departing from the spirit and scope of the invention. All such modifications and variations are intended to be included within the scope of the invention as defined in the appended claims rather than the specific embodiments that have been presented by way of example.

We claim:
1. A compound having the structure:

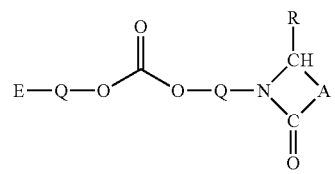

wherein:
E is a polymerizable moiety selected from the group consisting of: epoxides, (meth)acrylates, vinyl oxy and combinations thereof;
each Q is independently selected from the group consisting of alkylene, cycloalkylene, alkenylene, and arylene groups, wherein any of the groups may be with or without heteroatoms;
A is alkylene or alkenylene group comprising 2 to 50 carbon atoms, wherein 2 to 4 carbon atoms reside in a lactam ring between the

group and the

group; and
each R is independently selected from the group consisting of hydrogen, alkyl, cycloalkyl, alkenyl, and aryl groups, wherein any of the groups may be with or without heteroatoms.
2. A compound having a structure which is selected from the group consisting of:

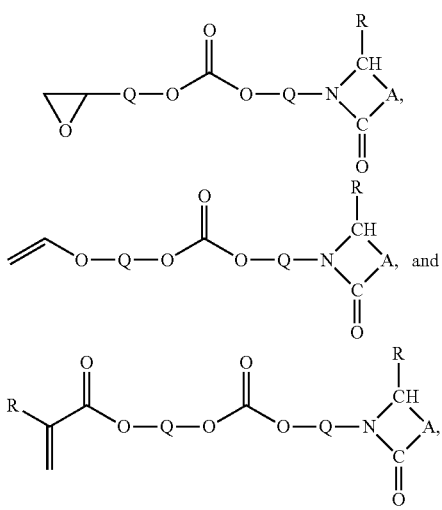

wherein:
each R is independently selected from the group consisting of hydrogen, alkyl, cycloalkyl, alkenyl, and aryl groups containing 1-10 carbon atoms, wherein any of the groups may be with or without heteroatoms;

A is selected from the group consisting of $$-\underset{H_2}{C}-\underset{H_2}{C}- \quad \text{or} \quad -\underset{H_2}{C}-\underset{H_2}{C}-\underset{H_2}{C}-\underset{H_2}{C}-;$$

and each Q is independently selected from the group consisting of alkylene, cycloalkylene, alkenylene, and arylene groups containing 1-10 carbon atoms, wherein any of the groups may be with or without heteroatoms.

3. The compound according to claim 2 that is

4. A composition comprising a compound of claim 1.

5. The composition according to claim 4 wherein the composition is an adhesive, coating, encapsulation, personal care, oilfield, membrane, agricultural, or cleaning composition.

* * * * *